United States Patent [19]

Miyano et al.

[11] Patent Number: 4,617,401
[45] Date of Patent: Oct. 14, 1986

[54] 8-SUBSTITUTED PYRROLIZIDINE AND QUATERNARY AMMONIUM SALTS THEREOF

[75] Inventors: Seiji Miyano; Kunihiro Sumoto, both of Fukuoka; Minoru Morita, Osaka; Fumio Sato, Kyoto, all of Japan

[73] Assignee: Suntory Ltd., Osaka, Japan

[21] Appl. No.: 574,932

[22] Filed: Jan. 27, 1984

Related U.S. Application Data

[63] Continuation of Ser. No. 376,240, May 7, 1982, abandoned, which is a continuation-in-part of Ser. No. 258,479, Apr. 28, 1981, abandoned.

[30] Foreign Application Priority Data

May 7, 1980 [JP] Japan .................................. 55-61095

[51] Int. Cl.$^4$ .......................................... C07D 209/52
[52] U.S. Cl. .................................. 548/453; 546/272; 514/339;
[58] Field of Search ................. 548/453; 546/272

[56] References Cited

U.S. PATENT DOCUMENTS 3,544,590 12/1970 Kiddleson ........................ 548/453

OTHER PUBLICATIONS

Miyano et al., C.A. 95:61903e, 1981.
Barton et al., Chem. Abs. 99487t, vol. 76, 1972.
Leonard et al., J.A.C.S. vol. 70, p. 2504, 1948.
Frantisek Sorm et al., Chem. Abs. p. 292, vol. 49.

*Primary Examiner*—Jane T. Fan
*Attorney, Agent, or Firm*—Burgess, Ryan & Wayne

[57] ABSTRACT

Novel 8-substituted pyrrolizidines and quaternary ammonium salts thereof of the formula

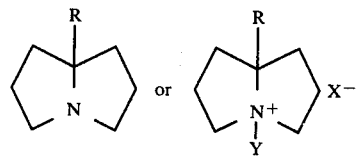

wherein R is a $C_4$-$C_{10}$ alkyl, aralkyl or aryl group; a lower alkoxycarbonyl or a lower alkoxycarbonylmethyl group; a lower aliphatic carboxyl group amidated with pyridinylamine, aniline, cyclohexylamine, phenylbenzylamine or methoxyphenylbenzylamine; a lower hydroxyalkyl group which has one or two phenyl, a trihalomethylphenyl or a halophenyl group; a lower alkyl group which has a hydroxyl group esterified with acetic, benzoic, cinnamic, xanthene-carboxylic or methoxybenzoic acid, or etherified with a $C_2$-$C_{13}$ alcohol; a lower alkyl group having a primary amino, a lower alkylamino, guanidino, benzylamino, hydroxylbenzylamino, methoxybenzylamino, aminobenzylamino, acetamino, benzoylamino, hydroxybenzoylamino, methoxybenzoylamino, or aminobenzoylamino group; or a lower alkyl group bearing benzoyl, methoxybenzoyl or halobenzoyl group; Y stands for an alkyl group quaternizing the nitrogen of the pyrrolizidine nucleus, which may optionally be substituted with halogen, an aryl, phenacyl or phenylphenacyl group; X stands for halogen. These compounds have various pharmacological activities such as atropine-like activity, papaverine-like activity, neuromuscular-blocking activity, etc.

7 Claims, No Drawings

8-SUBSTITUTED PYRROLIZIDINE AND QUATERNARY AMMONIUM SALTS THEREOF

This application is a continuation of application Ser. No. 376,240, filed May 7, 1982, now abandoned which is a continuation-in-part of Ser. No. 258,479, filed Apr. 28, 1982, now abandoned.

The present invention relates to novel 8-substituted pyrrolizidines and quarternary ammonium salts thereof.

In regard to pyrrolizidine derivatives which have a substituent at 8-position of the pyrrolizidine nucleus, there were reported 8-methylpyrrolizidine, 8-hydroxymethylpyrrolizidine, 8-chloromethylpyrrolizidine (Nelson et al., J.A.C.S., Vol. 71, 1949, 1762) and 8-cyanopyrrolizidine (Miyano et al. Synthesis, 1978, 701). No further development has been reported on the modification of the substituent.

The present inventors have successfully carried out much work on producing novel pyrrolizidine derivatives having various substituents at the 8-position, and found that these derivatives exhibit medicinally useful activities.

The object of the present invention is to provide novel pyrrolizidine derivatives and the production methods thereof.

The present invention is directed to 8-substituted pyrrolizidine and a quaternary ammonium salt thereof shown by the formula

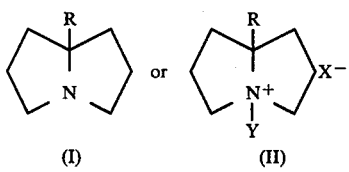

wherein R stand for a $C_1$–$C_{10}$ hydrocarbon group, a lower aliphatic carboxyl group esterified with a lower alcohol, a lower aliphatic carboxyl group amidated with a $C_5$–$C_{13}$ primary or secondary amine, a $C_2$–$C_{14}$ lower alkyl group which has a hydroxyl group and has optionally aryl substituents, a lower alkyl group which has hydroxyl group esterified with a $C_2$–$C_{15}$ carboxylic acid or etherified with a $C_2$–$C_{13}$ alcohol, a lower alkyl group having a primary amino group or a $C_1$–$C_{14}$ mono- or di-substituted amino group, or a lower alkyl bearing a $C_2$–$C_{10}$ acyl group; Y stands for an alkyl group quarternizing the nitrogen atom of the pyrrolizidine nucleus, which may optionally be substituted with halogen or an aromatic group, and X stands for halogen.

Referring to the definition of the above-mentioned R, the following explanation is given.

The $C_1$–$C_{10}$ hydrocarbon group may be aliphatic or aromatic. Of the aliphatic ones, methyl, ethyl, propyl, butyl or pentyl are mentioned. These alkyl groups may be straight-chained or branched ones such as isopropyl, isobutyl, tertiary butyl and isopentyl. The aliphatic group may also be alkenyl such as propenyl (allyl), butenyl and pentenyl. The above-mentioned aliphatic groups may have up to about ten carbon atoms, but a lower alkyl or lower alkenyl, whose carbon number is not more than 5, is preferable. The aromatic group is typically aralkyl or aryl, and, as the aralkyl group, a lower alkyl having a phenyl group, e.g. penzyl, phenethyl or phenylpropyl, is preferable. A typical example of the aryl group is phenyl.

As the lower aliphatic carboxyl group esterified with a lower alcohol, there may be mentioned lower alkoxycarbonyl, lower alkoxycarbonylmethyl and the like.

Referring to the lower aliphatic carboxyl group amidated with a primary or secondary amine of $C_5$–$C_{13}$, the primary amine may be exemplified heterocyclic amine, e.g. pyridinylamine, an aromatic amine e.g. aniline or an aliphatic amine e.g. cyclohexylamine, and the secondary amine may be exemplified by phenylbenzylamine, methoxyphenylbenzylamine and the like. The lower aliphatic carboxylic group to be amidated may be exemplified by carboxyl group, carboxymethyl and the like. As the examples of the lower aliphatic carboxyl groups amidated with the above-mentioned primary or secondary amine, there may be mentioned pyridinylaminocarboxyl, N-benzyl-N-phenylaminocarbonyl, N-benzyl-N-(4'-methoxyphenyl)aminocarbonyl, cyclohexylaminocarbonyl and anilinocarbonylmethyl.

As the lower alkyl group of $C_2$–$C_{14}$ having hydroxyl group and substituted or unsubstituted with aryl group, there may be mentioned hydroxymethyl, hydroxyethyl, hydroxybutyl, 2-hydroxy-2-phenylethyl, diphenylhydroxymethyl, 2,2-diphenyl-2-hydroxyethyl, bis(3-chlorophenyl)hydroxymethyl, bis(3-trifluoromethylphenyl)hydroxymethyl, 2-bis(3'-chlorophenyl)hydroxyethyl, 2-bis(3'-trichloromethylphenyl)hydroxyethyl groups, and the like.

The lower alkyl group having a hydroxyl group esterified with a $C_2$–$C_{15}$ carboxylic acid may be exemplified by acetoxymethyl, benzoyloxymethyl, cinnamoyloxymethyl, xanthene-9-carboxymethyl, 2-benzoyloxyethyl, 2-(4'-methoxybenzoyl)oxyethyl, 2-acetoxyethyl and 2-(xanthene-9'-carboxy)ethyl.

The lower alkyl group having a hydroxyl group etherified with a $C_2$–$C_{13}$ alcohol may be exemplified by methoxymethyl, 2-methoxyethyl, benzyloxymethyl, 2-benzyloxyethyl, diphenylmethyloxymethyl and 2-diphenylmethyloxyethyl.

Among the lower alkyls having primary amino group or $C_1$–$C_{14}$ mono- or di-substituted amino group, examples of those having primary amino group are aminomethyl and aminoethyl groups, and the examples of those having a mono-substituted amino group are the lower alkyl groups aminated with aliphatic or aromatic primary amine such as methylaminomethyl, guanydinomethyl, 2-guanydinoethyl, benzylaminomethyl, 2-benzylaminoethyl, hydroxy (or methoxy) benzylaminomethyl, aminobenzylaminomethyl or pyridinylaminomethyl as well as those having an acylamino group such as acetaminomethyl, 2-acetaminoethyl, benzoylaminomethyl, hydroxy (or methoxy) benzoylaminomethyl and aminobenzoylaminomethyl. As examples of those having a di-substituted amino group are mentioned the lower alkyl groups having tertiary amino groups of aliphatic, aromatic aliphatic or aromatic groups such as N,N-dimethylaminomethyl, 2-(N,N-dimethylamino)ethyl, N-methyl-N-benzylaminomethyl, N-benzyl-N-methoxyphenylaminomethyl, N-benzyl-N-phenylaminoethyl, 2-(N-benzoyl-N-phenylamino)ethyl, N-(2'-pyridyl)-N-benzoylaminomethyl groups.

The lower alkyl bearing acyl groups whose chain length is $C_2$–$C_{10}$ may be exemplified by benzoylmethyl, 2-benzoylethyl, methyl (or trifluoromethyl) benzoylmethyl or halobenzoylmethyl. Alkyl groups having an aliphatic acyl group such as acetoxymethyl or 2-propionylethyl may be employed, but the alkyl groups having aromatic acyl groups such as mentioned above are preferable.

The pyrrolizidine nucleus, as apparent from formula (I), has a tertiary nitrogen, which can readily be quaternized by a per se known method. Y in the formula (II) denotes an alkyl group for quaternizing the said nitrogen atom. The alkyl group is preferably a lower alkyl group such as methyl, ethyl, propyl or butyl, which may be haloalkyl group, substituted with a halogen, e.g. bromoethyl, bromopropyl, bromobutyl. The said alkyl groups, preferably lower alkyl groups, may be substituted with an aromatic group such as aryl or aromatic acyl. As examples substituted with aryl group, benzyl or phenethyl may be mentioned. The aromatic acyl group is preferably that of $C_6$-$C_{12}$. As examples substituted with such an acyl group, there may be mentioned phenacyl or phenylphenacyl. X stands for a halogen such as chlorine, bromine or iodine.

Among the compounds shown by the afore-mentioned formula (I), those in which R stands for a $C_1$-$C_{10}$ hydrocarbon group can be prepared by, for example, allowing 4,8-dehydropyrrolizinium perchlorate (III) (Miyano et al., Synthesis, 1978, 701) to react with Grignard's reagent derived from alkyl, aralkyl or arylhalide, or with an alkyl or aryl alkali metal compounds such as methyl lithium, butyl lithium or phenyl lithium.

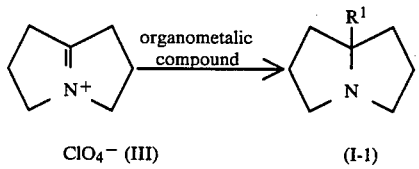

(wherein $R^1$ stands for a $C_{14}$-$C_{10}$ hydrocarbon group)

The reaction is conducted in an anhydrous solvent such as ether, tetrahydrofuran or dioxane, and it is accelerated by heating. It is generally preferable to carry out the reaction at reflux temperature.

Among the compounds representable by formula (I), those in which R stands for a lower aliphatic carboxylic acid group esterified with a lower alcohol can be prepared by subjecting the compound shown by formula (IV) below to alcoholsis in a lower alcohol.

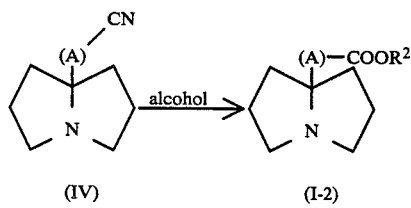

(wherein (A) stands for a lower alkylene group which may be present, and $R_2$ stands for a lower alkyl group)
The reaction usually proceeds under healing in the presence of a mineral acid such as hydrochloris or sulfuric acid.

Examples of the lower alcohol are methanol, ethanol, propanol, butanol, etc. Depending on the alcohol employed, corresponding alkyl esters are obtained.

Among the compounds shown by the formula (IV), 8-cyanopyrrolizidine having no lower alkylene group shown by (A) is known (Miyano et al., ibid.), while 8-cyano lower alkyl pyrrolizidines in which a lower alkylene group exists can be prepared by allowing a compound of the afore-mentioned type (III) or the free base thereof to react with a cyano lower aliphatic carboxylic acid.

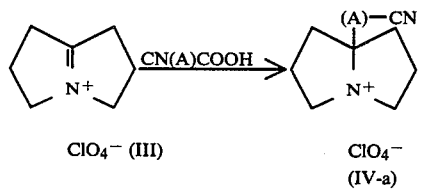

(in the formula, A stands for a lower alkylene group)
The reaction is conducted in a solvent such as dioxane, employing the free base as it is on perchlorite (III) in the presence of an alkali such as sodium carbonate, sodium hydroxide or potassium hydroxide, and these reactions can be accelerated by heating. It is desirable to use one equivalent of the above-mentioned alkali.

In formula (I), the compound (I-3) in which R is amidated with a $C_5$-$C_{13}$ primary or secondary amine can be prepared by allowing the compound shown by formula (I-2), below, to react with any of the afore-mentioned amines.

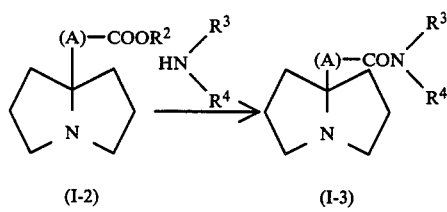

(in the formulae, (A) and $R_2$ are as previously defined, and

denotes a primary or secondary amine.)

The reaction can be carried out by subjecting a compound of the formula (I-2) and the amine to fusion, or by treating the amine with an alkali metal compound, such as sodium hydride, sodium amide or butyl lithium in an anhydrous solvent e.g. ether, tetrahydrofuran, dioxane or benzene, forming an alkalimetal salt of the amine, following by allowing it to react with a compound of the formula (I-2).

In formula (I), compounds in which R is a $C_2$-$C_{14}$ lower alkyl group having a hydroxyl group and unsubstituted or substituted with aryl can be prepared by the following method.

In the case where R is a lower alky group having a hydroxyl group, compound (I-4) can be prepared by subjecting the said compound (I-2) to reduction.

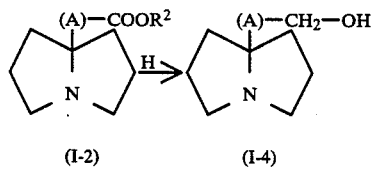

(wherein (A) is of the same meaning as defined above)

As examples of compounds of the formula (I-2), there may be mentioned, for example, 8-methoxycarbonylpyrrolizidine, 8-ethoxycarbonylpyrrolizidine, 8-methoxycarbonylmethylpyrrolizidine, 8-ethoxycarbonylmethylpyrrolizidine or 8-methoxycarbonylethylpyrrolizidine. The reduction is usually carried out by using a metal hydride such as lithium aluminium hydride in an anhydrous solvent e.g. ether, tetrahydrofuran or dioxane.

This reaction proceeds under mild conditions, for example, at a room temperature or at the refluxing temperature of the solvent then employed.

Thus, for example, 8-hydroxymethylpyrrolizidine, 8-(2hydroxyethyl)pyrrolizidine or 8-(3-hydroxpropyl)pyrrolizidine can be obtained. In the case where R is a lower alkyl group having hydroxyl and an aryl substituent, the following method is employed. In this way, compounds, in which R is a lower alkyl group whose hydroxyl group is attached not to the terminal carbon of the group but to an intermediate position, can also be obtained.

Practically, the target compounds can be obtained by allowing a compound of the formula (I-2) to react with a Gringnard's reagent prepared from a lower alkyl, aralkyl or aryl halide and magnesium or with an organic alkali metal compound, e.g. alkyl lithium or aryl lithium.

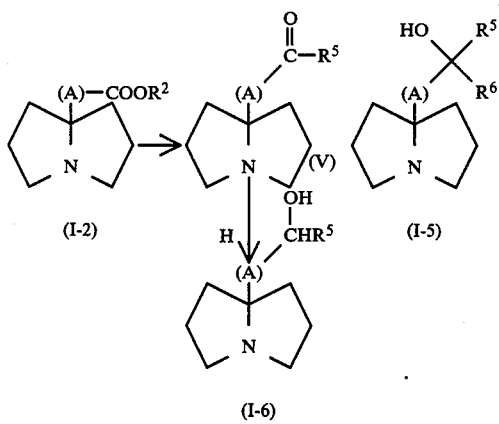

(in the formulae, (A) and $R_2$ are of the some meaning as defined above, and $R_5$ and $R_6$ respectively stand for a lower alkyl, aralkyl or aryl group)

The reaction is conducted in an anhydrous solvent such as ether, tetrahydrofuran or dioxane. By the above reaction are produced 8-acyl (or acyl lower alkyl) pyrrolizidine (V) and 8-disubstituted hydroxy lower alkyl pyrrolizidine (I-5), and these compounds can be easily purified by column-chromatography or fractional recrystallization.

Reduction of 8-acyl (or acyl lower alkyl) pyrrolizidine give 8-monosubstituted hydroxy lower alkyl pyrrolizidine (I-6).

Among the compounds represented by the formula (I), those in which R is a lower alkyl having a hydroxyl group esterified with a $C_2$–$C_{15}$ carboxylic acid can be prepared by allowing a compound of the above-mentioned (I-4), (I-5) or (I-6) to react with a halide of a $C_2$–$C_9$ carboxylic acid or with an anhydride thereof. The reaction is conducted in a solvent such as ether, benzene or chloroform in the presence or absence of an inorganic base, e.g. sodium hydroxide or sodium carbonate, or an organic base, e.g. triethylamine or pyridine.

According to the above method, the hydroxyl group of the compounds (I-4, I-5, I-6) can be esterified.

Among the compounds represented by the formula (I), those in which R is a lower alkyl group having a hydroxyl group etherified with $C_2$–$C_{13}$ alcohol can be prepared by either of the following processes (a) or (b).

(a): A compound (I-4), (I-5) or (I-6) is allowed to react with a halogenating agent to give a halogenide or with various sulfonyl halides to give the corresponding sulfonic acid ester compound, followed by subjecting these compounds to reaction with a metal alcoholate ($C_2$–$C_{13}$). As the halogenating agent, employable are for example thionyl chloride, oxalyl chloride, phosphorus trichloride, phosphorus pentachloride or phosphorus tribromide, and as the sulfonyl halides, employable are methanesulfonyl chloride or p-toluenesulfonyl chloride. The halogenation reaction is carried out in a solvent such as ether, benzene or chloroform, or without employing a solvent. The sulfonic acid esterification is conducted in a solvent such as ether, benzene or chloroform at a room temperature or at an elevated temperature. The reaction of the halogenide or the sulfonic acid ester compound thus obtained with a metal alcoholate can be accomplished in a solvent e.g. tetrahydrofuran, dioxane or toluene. The alcholoate can be prepared by, for example, allowing alcohol e.g. methanol, benzyl alcohol or benzhydrol to react with an alkali metal compound e.g. sodium hydride, sodium amide or butyl lithium in a solvent such as tetrahydrofuran, dioxane or toluene.

(b): A metal alcoholate of the compound (I-4), (I-5) or (I-6) is allowed to react with a halide or a $C_2$–$C_{13}$ alcohol. One of the above-mentioned compounds is allowed to react with the said alkali metal compound to afford a metal alcoholate. The halide of the alcohol is exemplified by methyl iodide, benzyl chloride or benzhydryl bromide.

Among the compounds shown by formula (I), compounds in which R is a lower alkyl group having amino can be prepared by subjecting a compound of the formula (IV) to reduction.

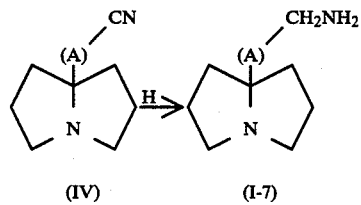

(in which (A) is as defined above)

The reducton is carried out by using a metal hydride e.g. lithium aluminium hydride in an anhydrous solvent such as ester, tetrahydrofuran or dioxane. The reduction can be effected by a catalitic reduction. In this case, as the catalyst, there may be employed nickel or palladium, and the reaction is conducted in a solvent such as slcohol e.g. methanol or ethanol, acetic acid or acetic acid ester.

Among the compounds shown by formula (I), compounds in which R is a lower alkyl group having mono- or di-substituted amine can be prepared by the following methods.

(c): An aminomethyl compound of the formula (I-7) is subjected to reductive alkylation by allowing the above compound to react with formaldehyde in e.g. formic acid (other aldehyde of the desired carbon number can similarly be employed), following by further allowing with a reducing agent such as sodium borohydride, preferably in an alcoholic solvent e.g. methanol, ethanol or propanol. Thus, compound of formula (I-8) can be obtained.

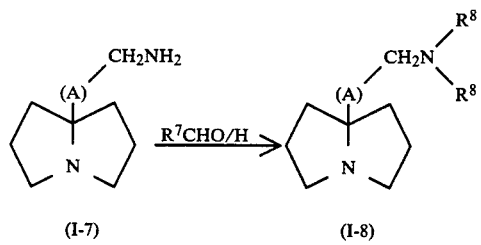

(in the formula, (A) is of the same meaning as defined above, $R^7CHO$ stands for aldehyde and at least one of the two $R^8$s stands for $-CH_2R^7$ and the other, if there is, denotes hydrogen)

(d): By allowing S-substituted isothiourea to react with a compound of the formula (I-7), the compound (I-9) which corresponds to that in which the aminomethyl group is converted to guandinomethyl group, is obtained.

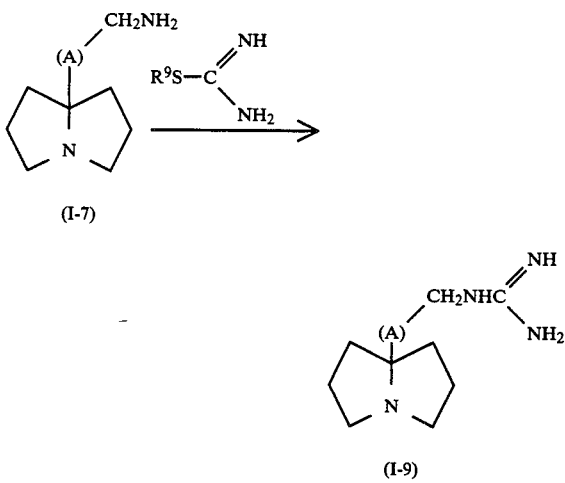

(in the formula, (A) is as defined above, and $R^9$ stands for alkyl group)

As the S-substituted thiourea, a salt of S-methyl thiourea can usually be employed, and the reaction is conducted in a solvent e.g. ethanol under heating.

(e): By subjecting a compound of the formula (I-7) or a compound of formula (I-8') which corresponds to that in which the

of a compound of the formula (I-8) is a residual group of a primary amine to acylation using an aliphatic or aromatic carboxylic acid or a reactive derivative thereof, is obtained the compound of formula (I-10).

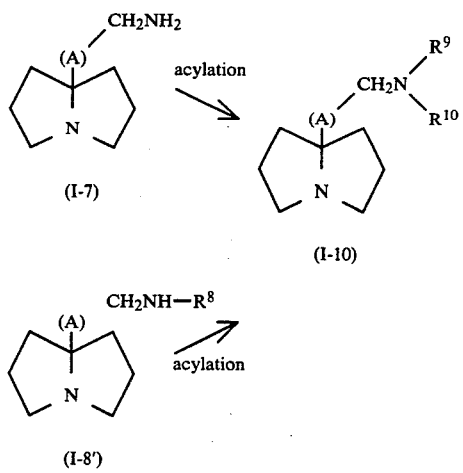

(In the formulae, (A) is of the same meaning as defined above, $NH-R^8$ stands for a residual group of primary amine, is a mono-or di-acylated amino group, and at least one of $R_9$ and $R_{10}$ is an acyl group and the other, if there is, denotes hydrogen or the same group as $R^8$)

The acylation is carried out by fusing a compound of (I-7) or (I-8') with a carboxylic acid or its ester, or by allowing a halide of the carboxylic acid or the carboxylic acid anhydride to react with the said compounds. As the carboxylic acid ester employable in the fusion reaction, practically preferable may be mentioned a lower alkyl ester such as methyl ester or ethyl ester.

The reaction employing carboxylic acid halide or anhydride is carried out in an inert solvent, e.g. ether benzene, dichloromethane or chloroform.

As the base, there may be employed an inorganic or organic base, e.g. alkali hydroxide, triethylamine or pyridine, but the reaction can proceed without employing a base.

(f): Reduction of a compound of formula (I-10) gives a compound of formula (I-11).

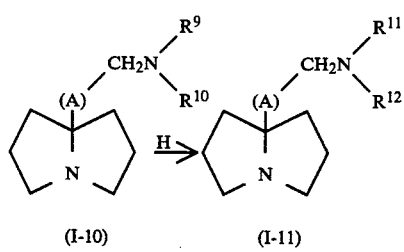

(in the formula, (A), $R^9$ and $R^{10}$ are as defined above, and

stands for a primary or secondary amine residue)

The reaction is carried out by allowing the said compound (I-10) to react with a metal hydride such as lithium aluminium hydride in an anhydrous solvent e.g. ether tetrahydrofuran or dioxane. By this reaction, the carbonyl group of the acyl group contained in $R^9$ and/or $R_{10}$ of the compound (I-10) is reduced to methylene group.

(g): Reduction of a compound of formula (I-3) affords a compound of formula (I-12).

$$(I-3) \longrightarrow (I-12)$$

(in the formula, (A), $R^3$ and $R^4$ are of the same meaning as defined above)

The reduction is performed in an anhydrous solvent e.g. ether, tetrahydrofuran or dioxane using a metal hydride, for example, lithium aluminium hydride, thereby the carbonyl group of the compound (I-3) is reduced to methylene group.

Among the compounds of formula (I), those in which R is a lower alkyl group having a $C_2$–$C_{10}$ acyl group can be obtained, as referred to in the preparation of the compounds of formulae (I-5) and (I-6), by allowing an ester compound of the formula (I-2') to react with a Gringnard's reagent prepared from a $C_1$–$C_9$ alkyl, aralkyl or aryl halide and magnesium, or with an organic alkali metal compound such as $C_1$–$C_9$ alkyl, aralkyl or aryl lithium.

$$(I-2') \longrightarrow (I-13) + (I-14)$$

(in the formula, A stands for a lower alkylene group, $R^2$ is as defined above, and $R^{13}$ and $R^{14}$ respectively stand for $C_1$–$C_9$ alkyl, aralkyl or aryl)

The reaction is carried out in an anhydrous solvent e.g. ether, tetrahydrofuran or dioxane.

As the $C_1$–$C_9$ alkyl, aralkyl or aryl groups, there may, for example, be mentioned methyl, ethyl, benzyl, phenyl, methylphenyl, trifluoromethylphenyl or chlorophenyl.

This reaction affords 8-acyl lower alkyl pyrrolizidines (I-13) and 8-disubstituted hydroxylower alkyl pyrrolizidines (I-14), and these compounds can be easily separated from each other by means of fractional crystallization or column chromatography.

The compounds of the formula (I) can be easily converted to the corresponding quaternary ammonium salts by conventional method.

The conversion reaction is carried out by allowing a compound (I) to react with an alkyl halide having or not having a halogen substituent or an aromatic substituent. It is usually preferable to perform the reaction under heating in a solvent such as methanol, ethanol or sulfonane.

$$(I) \xrightarrow{YX} (II)$$

(in the formulae, R, Y and X are respectively as defined above)

As the alkyl halide, preferable are, for example, halides of a lower alkyl such as methyl, ethyl, propyl or butyl, and, when desired, pentyl, hexyl or an alkyl halide of longer carbon chain may be employed.

The halide is usually chloride, bromide or iodide.

The alkyl halide having a halogen substituent, may be exemplified by the halide of methyl iodide, propyl bromide or butyl bromide.

The alkyl halide substituted with an aromatic group may be exemplified by, the halides of aralkyls such as benzyl or phenethyl, and also by halides of alkyls having an aromatic acyl group such as phenacyl or phenylphenacyl. Since the quaternary ammonium salt resulting from this reaction generally precipitates as crystals, this is easily separable from the reaction mixture. Thus obtained 8-substituted pyrrolizidine derivatives of the formulae (I) and (II) are novel compounds having, for example, the following pharmacological activities.

(1) Spasmolytic activity on the smooth muscle of guinea pig ileum. This activity is, depending on the substituents, either atropine-like or papaverine-like.

(2) The compounds having papaverine-like activity have also coronary artery dilating activity in the isolated guinea pig preparation.

Depending on the nature of the compound, the following activities are observed.

(3) Anti-arrhythmic activity against aconitine-induced dysrhythmia (4) Neuromuscular-blocking activity (5) hypotensive activity against experimentally induced or spontaneously hypertensive rats (6) Platelet aggregation inhibiting activity (7) Antihistamine activity Utility of the compounds of the invention, dosages and means of administration are more particularly described in the following Table.

| UTILITY OF THE COMPOUNDS | | |
|---|---|---|
| Type of Activity | Indications | Dosages and Administration route |
| Atropin-like activity | Parkinsonismus; Peptic ulcer; Spasmolytica for Stomachalgia | 5–50 mg/day, Total 5 mg.–20 g., peroral |
| Papaverine-like activity | Asthma; Angina pectoris; Migraine; Peripheral vascular diseases accompanied by angiospasm. | 10–200 mg/day; Total, 1 mg–50 g (undefinable in asthma), peroral. |
| Neuromuscular-blocking activity | Muscular relaxation in narcosis; Diagnosis of Myasthenia. | 10–200 mg/time; Total, 10–200 mg, intravenous injection. |
| Anti-arrhythmic activity | Arrythmia | 20–500 mg/time; Total indefinite (for life), peroral; Intravenous injection at rate of 50 mg/hr (up to 500 mg). |
| Platelet aggregate inhibiting activity | Thrombosis; Prophylaxis for Thrombus | 500–1000 mg/time; Total 1,500 mg–500 g, three times/day, peroral. |
| Antihistamine activity | Urticaria; Allergic rhinitis; Drug Allergosis | 10–100 mg/time; Total, 50 mg–10 g, three times/day, peroral. |

The compound of this invention may each be orally administered as they are, as formulated with a pharmacologically acceptable carrier, excipient or diluent in the routine manner, in the dosage forms as powders, granules, dry syrup, tablets, capsules, or non-orally, for instance, as intravenous injection. The injection may be prepared by dissolving the 8-substituted pyrrolizidine in the form of hydrochoride or a quaternary ammonium salt into physiological saline solution.

These compounds are, therefore, of value as medicines.

The following examples are given for practical explanation of the present invention, but not for limitative purposes.

EXAMPLE 1

General procedure for producing 8-alkyl, allyl or aralkyl-substituted pyrrolizidine:

(A) One equivalent of 4,8-dehydropyrrolizidinium perchlorate was added to three equivalents of Grignard reagent prepared from alkyl halide, aryl halide or aralkyl halide with magnesium in anhydrous ether or anhydrous tetrahydrofuran, and the mixture was heated under reflux for two hours. The reaction mixture was stirred under ice-cooling to decompose an excess of Gringnard reagent with 20% sodium hydroxide solution. The organic layer was taken, washed with saturated sodium chloride solution, dried over anhydrous magnesium sulfate, and evaporated to give 8-alkyl, allyl or aralkyl-substituted pyrrolizidine. Thus obtained oily products were led to respective salts by a per se known method, and they are identified as crystals shown in Table 1 below.

TABLE 1

| Name of Compound | Yield (%) | Melting Point (°C.) |
|---|---|---|
| 8-Phenylpyrrolizidine perchlorate | 13–14 | 145.5–148 |
| 8-Benzylpyrrolizidine hydrobromide | 83.5 | 190.5–192 |
| 8-Phenethylpyrrolizidine picrate | 50 | 149–151 |
| 8-(3-Phenylpropyl)pyrrolizidine hydrochloride | 60 | 201–203 (decomp.) |

TABLE 1-continued

| Name of Compound | Yield (%) | Melting Point (°C.) |
|---|---|---|
| 8-Allylpyrrolizidine picrate | 79 | 153–160 (decomp.) |

Elemental Analysis (%)

8-Phenylpyrrolizidine perchlorate ($C_{13}H_{18}ClNO_4$). Calcd.: C 54.26, H 6.31, N 4.87. Found: C 54.20, H 6.28, N 4.84.

8-Benzylpyrrolizidine hydrobromide ($C_{14}H_{20}BrN$). Calcd.: C 59.58, H 7.14, N 4.96. Found: C 59.71, H 7.13, N 4.84.

8-Phenethylpyrrolizidine picrate ($C_{21}H_{24}N_4O_7$). Calcd.: C 56.75, H 5.44, N 12.61. Found: C 56.69, H 5.45, N 12.73.

8-(3-Phenylpropyl)pyrrolizidine hydrochloride ($C_{16}H_{24}ClN$). Calcd.: C 72.29, H 9.10, N 5.27. Found: C 72.10, H 9.15, N 5.26.

8-Allylpyrrolizidine picrate ($C_{16}H_{20}N_4O_7$). Calcd.: C 50.52, H 5.30, N 14.73. Found: C 50.13, H 5.27, N 14.36.

(B) To a suspension of 0.419 g of 4.8-dehydropyrrolizidinium perchlorate in 50 ml of anhydrous ether was added dropwise 3.42 ml. of n-butyllithium (15% hexane solution) under stirring at −28° C., followed by stirring for 4 hours at −23° C. The reaction mixture was treated as in the method (A) above to give 0.195 g (yield 58.3%) of 8-n-butylpyrrolizidine as colorless oil, of which picrate was yellow crystals, m.p. 92°–99.5° C.

Elemental Analysis (%): $C_{17}H_{24}N_4O_7$. Calcd.: C 51.51, H 6.10, N 14.14. Found: C51.59, H 6.14, N 13.97.

EXAMPLE 2

Preparation of 8-ethoxycarbonylpyrrolizidine

To 100 ml. of ethanol saturated with hydrogen chloride was added dropwise a solution of 13.49 g (99 m.mol.) of 8-cyanopyrrolizidine and water (1.78 ml, 99 m.mol.) in 40 ml of ethanol. The mixture was heated under reflux for 18 hours, then cooled with ice, and the resulting crystals are removed by filtration. The filtrate evaporated to leave an oil, which was dissolved in 80 ml. of 20% sodium hydroxide solution and extracted with chloroform three times. The chloroform layer was washed with saturated sodium chloride solution, dried over anhydrous magnesium sulfate, and evaporated to give 14.9 g (yield 82.1%) of 8-ethoxycarbonylpyrrolizidine as an oil.

$IR_{max}^{CHCl_3}$ cm$^{-1}$: 1720 (C=O).

NMR (CDCl$_3$)δ : 1.26 (3H triplet, J=7Hx, —CH$_2$—CH$_3$). 4.17 (2H quartet, J=7 Hz, —CH$_2$—CH$_3$).

This product was subjected to distillation under reduced pressure to give a colorless oil, b.p. 80°–81° C. (4 mmHg).

Elemental Andlysis (%): $C_{10}H_{17}NO_2$. Calcd.: C 65.54, H 9.35, N 7.64. Found: C 65.35, H 9.45, N 7.89.

EXAMPLE 3

Preparation of 8-methoxycarbonylpyrrolizidine

To a stirred solution 30 g. (0.2 mol.) of 8-cyanomthylpyrrolizidine in 300 ml. (7.4 mol.) of methanol was added dropwise 120 ml. (2.3 mol.) of concentrated sulfuric acid at room temperature, followed by reflux for 24 hours. The reaction mixture was neutralized with sodium hydrogen carbonate, basified with 20% sodium hydroxide solution, and extracted with chloroform. The chloroform layer was washed with saturated sodium chloride solution, dried over anhydrous magnesium sulfate, and evaporated to give an oil, which was subjected to distillation under reduced pressure to give 29 g. (80%) of 8-methoxycarbonylmethylpyrrolizidine as a colorless oil, b.p. 92°–93° C. (7 mmHg).

$IR_{max}^{CHCl_3}$ cm$^{-1}$: 1740 (C=O).

NMR(CDCl$_3$)δ : 2.43 (2H, singlet, —CH$_2$—COOCH$_3$). 3.63 (3H, singlet, —COOCH$_3$).

The product was converted to its hydrochloride as usual method, and recrystallized from isopropanol-ether to give colorless crystals.

m.p. 100°–103° C.

Elemental Analysis (%): C$_{10}$H$_{18}$ClNO.0.25H$_2$O. Calcd.: C 53.57, H 8.32, N 6.25. Found: C 53.59, H 8.71, N 6.21.

EXAMPLE 4

Preparation of 8-cyanomethylpyrrolizidine

A solution of 128 g (1.2 mol.) of 1.8-dehydropyrrolizidine and 152 g (1.8 mol.) of cyanoacetic acid in 1000 ml of dioxane was heated under reflux for 5 hours. The solvent was removed by evaporation to leave an oil, to which was added water, and the aqueous solution was extracted with ether. The ether layer was washed with saturated sodium chloride solution, dried over anhydrous magnesium sulfate, and evaporated to leave an oil, which was subjected to distillation under reduced pressure to give 114 g (yield 65%) of 8-cyanomethylpyrrolizidine as colorless oil, b.p. 113°–120° C. (11–12 mmHg).

$IR_{max}^{CHCl_3}$ cm$^{-1}$: 2250 (—C N).

NMR (CDCl$_3$)δ : 2.41 (2H, singlet, —CH$_2$—CN).

The product was converted to its hydrochloride as usual method, which was recrystallized from methanol-ether to give colorless crystals m.p. 140°–150° C. (sublime).

Elemental Analysis (%): C$_9$H$_{15}$ClN$_2$. Calcd.: C 57.90, H 8.10, N 15.01. Found: C 58.00, H 8.17, N 15.01.

EXAMPLE 5

(A) General procedure of 8-(N-substituted)aminocarbonylpyrrolizidine

To a stirred suspension of 1.5 equivalent of sodium hydride in anhydrous dioxane was added slowly 1 equivalent of 2-aminopyridine at room temperature, then the mixture was heated under reflux for 2 hours. While the reaction mixture was stirred under ice-cooling, one equivalent of 8-ethoxycarbonylpyrrolizidine dissolved in anhydrous dioxane was added thereto a little by little, and the mixture was heated under reflux for 3 hours. The reaction mixture was acidified with 10% hydrogen chloride solution under cooling with ice and washed with ether. The aqueous layer was basified with 20% sodium hydroxide solution, and extracted with chloroform. The chroform layer was washed with saturated sodium chloride solution, dried over anhydrous magnesium sulfate, and evaporated to give the oily compounds shown in Table 2 below.

TABLE 2

|  | 8-(N—cyclohexyl) aminocarbonyl-pyrrolizidine | 8-(N—2'-pyridinyl) aminocarbonyl-pyrrolizidine |
|---|---|---|
| Yield (%) | 33.6 | 62.4 |
| m.p. (°C.) | Oil | 55–56 |
| Elemental Analysis (%) | C$_{14}$H$_{24}$N$_2$O (free base) | C$_{13}$H$_{17}$N$_3$O (free base) |

TABLE 2-continued

|  | 8-(N—cyclohexyl) aminocarbonyl-pyrrolizidine | 8-(N—2'-pyridinyl) aminocarbonyl-pyrrolizidine |
|---|---|---|
| Calcd. |  |  |
| C | 71.14 | 67.50 |
| H | 10.24 | 7.41 |
| N | 11.85 | 18.17 |
| Found |  |  |
| C | 69.98 | 67.63 |
| H | 10.26 | 7.56 |
| N | 11.65 | 18.50 |
| IR | 3345 (—NH—) | 3280 (—NH—) |
| $v_{max}^{neat}$ cm$^{-1}$ | 1675 (>C=O) | 1695 (>C=O) |
| NMR δ (CDCl$_3$) | 7.37–8.38 (1H, brood singlet, —NH—) | 6.80–7.14 (1H, multiplet, pyridinyl H); 7.43–7.82 (1H, multiplet, H); 8.12–8.38 (2H, multiplet, H) |

(B) Preparation of 8-(N-benzyl-N-phenyl)aminocarbonylpyrrolizidine

To a stirred solution of 0.183 g. of N-benzylaniline in 10 ml. of anhydrous ether was slowly added 0.8 ml. of n-butyllithium (15% hexane solution) at −78° C. The reaction temperature was slowly raised up to room temperature. After the reaction solution was stirred for 2 hours at room temperature, a solution of 0.183 g. of 8-ethoxycarbonylpyrrolizidine in 20 ml of anhydrous ether was added dropwise to the reaction mixture. This was allowed to stand at room temperature for 2 hours and extracted with 10% hydrogen chloride solution. The aqueous layer was basified with a 20% sodium hydroxide solution followed by extraction with chloroform. The chloroform layer was washed with saturated sodium chloride solution, dried over anhydrous magnesium sulfate, and evaporated to leave an oil. The product was subjected to column chromatography using of 20 g. of alumina. The solid obtained from chloroform fraction was recrystallized from benzene-hexane to give 0.13 g (yield: 62.8%) of 8-(N-benzyl-N-phenyl-)aminocarbonylpyrrolizidine as colorless needles, m.p. 111°–112° C.

$IR_{max}^{neat}$ cm$^{-1}$: 1695 (C=O).

NMR(CDCl$_3$)δ : 4.85 (2H, singlet, —CH$_2$—C$_6$H$_5$).

(C) Preparation of 8-{N-benzyl-N-(4'-methoxyphenyl)}aminocarbonylpyrrolizidine To a stirred solution of 0.639 g (3 mmol.) of benzyl-paraanisidine in 20 ml of anhydrous tetrahydrofuran was added 2.2 ml (3.6 mmol) of n-butyllithium (15% hexane solution at −78° C. The reaction temperature was raised slowly up to a room temperature. The reaction mixture was stirred for 1.5 hours at a room temperature, and again cooled to −78° C., to which was added gradually a solution of 0.549 g. (3 mmol) of 8-ethoxycarbonylpyrrolizidine in 10 ml. of anhydrous tetrahydrofuran, followed by raising the temperature gradually up to a room temperature and stirring for two hours. The reaction mixture was processed as in (B) above. The resulting oil (1.014 g) was subjected to column chromatography using 100 g of alumina. From the chloroform fraction was oblained 0.655 g (yield: 62.3%) 8-N-benzyl-N-(4'-methoxyphenyl)aminocarbonylpyrrolizidine.

NMR(CDCl$_3$)δ : 3.75 (3H, singlet, —O—CH$_3$); 4.80 (2H, singlet, —C$\underline{H}_2$—C$_6$H$_5$); 6.83 (4H, singlet,

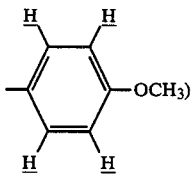

7.18 (5H, singlet, —C$_6$$\underline{H}_5$).

EXAMPLE 6

Preparation of 8-anilinocarbonylmethylpyrrolizidine

A mixture of 3.66 g (20 mmol) of 8-methoxycarbonylmethylpyrrolizidine and 19.8 g (200 mmol) of aniline were fused at 160°–170° C. for 23–26 hours, followed by removing an excess aniline to yield 5.53 g of a brown oil. This was converted to its hydrochloride as usual manner, which was recrystallized from ethanol-ether to give 3.03 g (yield: 54.0%) of 8-anilinocarboxymethylpyrrolizidine hydrochloride as colorless plates, m.p. 206°–207° C.

Elemental Analysis (%): C$_{15}$H$_{21}$ClN$_2$O. Calcd.: C 64.16, H 7.54, N 9.98. Found: C 64.19, H 7.60, N 9.88.

Free base of this product:

IR$_{max}^{CHCl_3}$ cm$^{-1}$ : 1670 (—CON).

NMR(CDCl$_3$)δ : 2.41 (2H, singlet, —CH$_2$CO—); 7.0–7.75 (5H, multiplet, C$_6$$\underline{H}_5$—); 10.8–11.3 (1$\underline{H}$, broad singlet, —N$\underline{H}$—).

EXAMPLE 7

(A) Preparation of 8-hydroxymethylpyrrolizidine

To a stirred suspension of 0.38 g (10 mmol.) of lithium aluminium hydride in 50 ml. of anhydrous ether was added dropwise 1.83 g (10 mmol) of 8-carboethoxypyrrolizidine under ice-cooling and this was heated under reflux for 2 hours. An excess lithium aluminium hydride was decomposed with 20% sodium hydroxide solution under ice-cooling. The organic layer was washed with saturated sodium chloride solution, dried over anhydrous magnesium sulfate, then the solvent was evaporated off to leave 1.07 g (yield: 75.7%) of 8-hydroxymethylpyrrolizidine as an oil.

IR$_{max}^{CHCl_3}$ cm$^{-1}$ : 3360 (—OH).

NMR(CDCl$_3$)δ : 3.27 (2H, singlet, —C$\underline{H}_2$—OH).

This product was led to its hydrochloride as usual method to give colorless prisms, m.p. 250° C.

Elemental Analysis (%): C$_8$H$_6$ClNO. Calcd.: C 54.08, H 9.08, N 7.88. Found: C 54.04, H 9.08, N 7.73.

(B) Preparation of 8-(2-hydroxyethyl)pyrrolizidine

To a stirred suspension of 8.0 g (0.21 mol.) of lithium aluminium hydride in 200 ml. of anhydrous ether was added dropwise a solution of 20.0 g (0.11 mol.) of 8-methoxycarbonylmethylpyrrolizidine in 100 ml. of anhydrous ether under ice-cooling, followed by stirring for further 16 hours at a room temperature. The reaction mixture was treated in a manner similar to the above to give 14.9 g (yield: 88%) of 8-(2-hydroxyethyl)-pyrrolizidine as colorless oil, b.p. 93.5°–94.5° C. (5 mmHg).

NMR(CDCl$_3$): 3.79 (2H, triplet, J=5 Hz, —C$\underline{H}_2$OH); 6.95 (1H, singlet, —CH$_2$O$\underline{H}$, disappeared by D$_2$O exchange).

This product was led to its picrate by a conventional manner, which was recrystallized from ethanol to yield yellow needles, m.p. 208°–211° C.

Elemental Analysis (%): C$_{15}$H$_{20}$N$_4$O$_8$. Calcd.: C 46.47, H 5.25, N 14.58. Found: C 46.89, H 5.24, N 14.60.

EXAMPLE 8

General procedure of producing 8-bis(3'-substituted phenyl)hydroxymethylpyrrolizidine To a stirred Gringnard reagent prepared from 2.5 equivalents of m-substituted bromobenzene and 3 equivalents of magnesium in anhydrous tetrahydrofuran was added 1 equivalent of 8-ethoxycarbonylpyrrolizidine under ice-cooling, then the mixture was heated under reflux for 4 hours. An excess Gringnard reagent was decomposed with tetrahydrofuran containing water under ice-cooling, followed by separation of the organic layer. The organic layer was washed with saturated sodium chloride solution, dried over anhydrous magnesium sulfate, and evaporated to yield the compounds as shown in Table 3 below:

TABLE 3

| | 8-Diphenylhydroxymethyl-pyrrolizidine | 8-Bis(3'-chlorophenyl)-hydroxymethylpyrrolizidine hydrochloride | 8-Bis(3'-trifluoromethyl-phenyl)hydroxymethyl-pyrrolizidinehydrochloride |
|---|---|---|---|
| Yield (%) | 59.6 | 68.8 | 62.1 |
| m.p. (°C.) | 103–106.5 | 246–248.5 | sublimation at ≧200° C. |
| Elemental Analysis (%) | C$_{20}$H$_{23}$NO | C$_{20}$H$_{22}$Cl$_3$NO | C$_{22}$H$_{22}$ClF$_6$NO |
| Calcd. | | | |
| C | 81.87 | 60.24 | 56.72 |
| H | 7.90 | 5.56 | 4.76 |
| N | 4.77 | 3.51 | 3.01 |
| Found | | | |

TABLE 3-continued

| | 8-Diphenylhydroxymethyl-pyrrolizidine | 8-Bis(3'-chlorophenyl)-hydroxymethylpyrrolizidine hydrochloride | 8-Bis(3'-trifluoromethyl-phenyl)hydroxymethyl-pyrrolizidinehydrochloride |
|---|---|---|---|
| C | 82.00 | 60.32 | 56.49 |
| H | 7.93 | 5.65 | 4.88 |
| N | 4.71 | 3.48 | 3.12 |
| $IR\nu_{max}^{KBr}$ cm$^{-1}$ | 3315(—OH) | 3300(—OH) | 3320(—OH) |
| NMRδ (CDCl$_3$) (Free base) | 7.10–7.70(10H, multiplet, —(C$_6$H$_5$)$_2$ | 6.92–7.53(8H, multiplet, 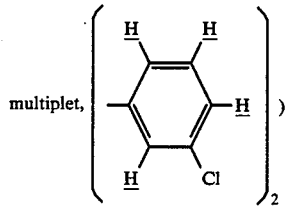) | 7.06–7.90(6H, multiplet, 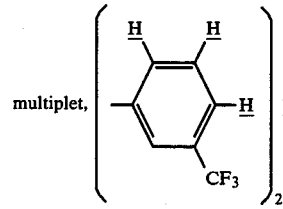), 7.80(2H, singlet, 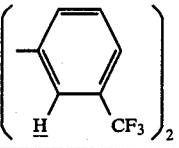) |

EXAMPLE 9

General procedure of preparing 8-{2'-bis(3''-substituted phenyl)-2'-hydroxyethyl}pyrrolizidine and 8-(3'-substituted phenyl)carbonylmethylpyrrolizidine To a Grignard's reagent prepared from 5 equivalents of m-substituted bromobenzene and 6 equivalents of magnesium in anhydrous tetrahydrofuran was added dropwise 1 equivalent of 8-methoxycarbonylmethyl-pyrrolizidine dissolved in anhydrous tetrahydrofuran, then the mixture was heated under reflux for 3 hours. An excess Gringnard's reagent was decomposed with 20% sodium hydroxide solution under ice-cooling followed by separation of the organic layer. The organic layer was washed with saturated sodium chloride solution, dried over anhydrous magnesium sulfate, and evaporated to give solid, which was recrystallized from methanol to give the compounds shown in Table 4 below.

The residue obtained by evaporating off the mother liquor was led to its hydrobromide or hydrochloride by conventional manner, which was recrystallized from ethanol-ether to give the compounds shown in Table 5 below.

TABLE 4

| | 8-(2',2'-diphenyl-2'-hydroxylethyl)pyrrolizidine | 8-{2'-bis(3''-chlorophenyl)-2'-hydroxyethyl}pyrrolizidine | 8-2'-bis(3''-trifluoro-methylphenyl)-2'-hydroxyethyl pyrrdizidine |
|---|---|---|---|
| Yield (%) | 14.9 | 39.6 | 35.9 |
| m.p. (°C.) | | | |
| Hydrochloride | — | 306–308 (decomp.) | 267–269 (decomp.) |
| Free base | 172–173 | — | — |
| Elemental Anaylsis (%) | C$_{21}$H$_{25}$NO | C$_{21}$H$_{24}$Cl$_3$NO | C$_{23}$H$_{24}$ClF$_6$NO |
| Calcd. | | | |
| C | 82.04 | 61.10 | 57.56 |
| H | 8.20 | 5.86 | 5.04 |
| N | 4.56 | 3.39 | 2.92 |
| Found | | | |
| C | 82.02 | 61.08 | 57.30 |
| H | 8.22 | 5.97 | 5.24 |
| N | 4.37 | 3.25 | 2.75 |
| NMRδ | 7.0–7.7(10H, multiplet, —(C$_6$H$_5$)$_2$) | | 7.4–7.8(8H, multiplet 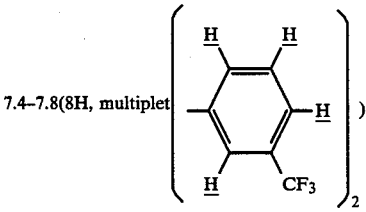) |

TABLE 5

| | 8-phenylcarbonylmethyl-pyrrolizidine | 8-(3'-chlorophenyl)carbonyl-methylpyrrolizidine | 8-(3'-trifluoromethylphenyl)carbonylmethylpyrrolizidine |
|---|---|---|---|
| Yield (%) | 34.5 | 16.6 | 10.7 |
| m.p. (°C.) | 174–176 (hydrobromide) | 174–176 (hydrochloride) | 133–135 (hydrochloride) |
| $IR\nu_{max}^{KBr} cm^{-1}$ | 1690 (\C=O/) | 1680 (\C=O/) | 1700 (\C=O/) |
| NMRδ (CDCl$_3$) | 3.9(2H, singlet, —C$\underline{H}_2$—CO—) 7.3–7.5(3H, multiplet, 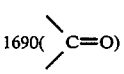) 7.9–8.1(2H, multiplet, 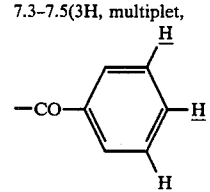) | 3.9(2H, singlet, —C$\underline{H}_2$—CO—) 7.3–7.5(2H, multiplet, 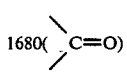) 7.8–8.0(2H, multiplet, 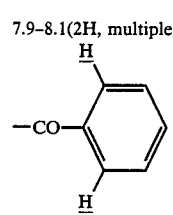) | 4.0(2H, singlet, —C$\underline{H}_2$—CO—) 7.4–7.8(2H, multiplet, 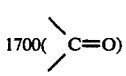) 8.3(2H, multiplet, 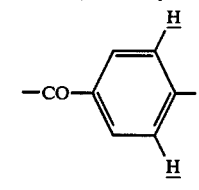) |
| Elemental Analysis (%) | C$_{15}$H$_{20}$BrNO | C$_{15}$H$_{19}$Cl$_2$NO | C$_{16}$H$_{19}$ClF$_3$NO |
| Calcd. | | | |
| C | 58.07 | 60.01 | 57.57 |
| H | 6.50 | 6.38 | 5.74 |
| N | 4.52 | 4.67 | 4.20 |
| Found | | | |
| C | 57.83 | 60.25 | 57.37 |
| H | 6.52 | 6.52 | 5.88 |
| N | 4.37 | 4.39 | 4.31 |

EXAMPLE 10

Preparation of 8-}(2'-hydroxy-2'-phenyl)ethyl}pyrrolizidine

To a stirred solution of 1.00 g of 8-phenylcarbonylmethylpyrrolizidine hydrobromide in 30 ml of methanol was added 0.60 g of sodium borohydride under ice-cooling and the mixture was stirred for 2 hours at a room temperature. The solvent was evaporated, and water was added to the residue. The mixture was subjected to extraction with chloroform. The chloroform layer was washed with a saturated sodium chloride solution, dried over anhydrous magnesium sulfate, and evaporated. The residue was converted to the corresponding hydrochloride as usual, which was recrystallized from ethanol-ether to yield 0.66 g (yield: 76%) of 8-{(2'-hydroxy-2'-phenyl)ethyl}pyrrolizidine hydrochloride as colorless crystal.

Elemental Analysis (%): C$_{15}$H$_{22}$ClNO Calcd.: C 67.27, H 8.28, N 5.23 Found: C 67.26, H 8.33, N 5.13

Free base of this product:

NMR(CDCl$_3$): 4.92 (1H, triplet, J=6 Hz, —CH$_2$—C$\underline{H}$OH—).

EXAMPLE 11

(A) General procedure 8-acyloxymethylpyrrolizidine

To stirred solution of 1 equivalent of acid chloride in benzene was added dropwise slowly 1 equivalent of 8-hydroxymethylpyrrolizidine at a room temperature, and stirring was continued for 6–10 hours. The residue obtained by removing the solvent was recrystallized from ethanol-ether to yield the hydrochlorides of the desired products shown in Table 6 below.

TABLE 6

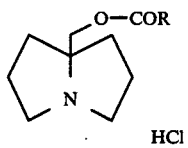
HCl

| Compound No. | R | Yield (%) | m.p. (°C.) | NMR(CDCl₃)δ Free Base | IR$\nu_{max}$cm$^{-1}$ | Elemental Analysis (%) Calcd. | Found |
|---|---|---|---|---|---|---|---|
| (1) | —CH₃ | 87 | hygroscopic | 2.05(3H, singlet —O—COC$\underline{H}$₃) | 1735($\diagdown$C=O) | C₁₀H₁₇NO₂(free base) C 65.54 H 9.35 N 7.64 | C 65.38 H 9.52 N 7.48 |
| (2) | phenyl | 90 | 148–153.5 | 4.65(2H, singlet, —CH₂—O—CO—) 7.13–7.78(3H, multiplet) [—CO— with H's shown] 7.98–8.28(2H, multiplet) | 1719($\diagdown$C=O) | C₁₅H₂₀ClNO₂·0.5H₂O C 61.95 H 7.27 N 4.82 | C 62.01 H 7.43 N 5.36 |
| (3) | —CH=CH—phenyl | 73 | 129–133 | 4.55(2H, singlet, —C$\underline{H}$₂—O—CO—) 6.45(1H, doublet, J=16Hz =C$\underline{H}$—ph) 7.81(1H, doublet, J=16Hz —C$\underline{H}$=ch—ph) | 1720($\diagdown$C=O) | C₁₇H₂₂ClNO₂·0.5H₂O C 64.44 H 7.32 N 4.42 | C 64.54 H 7.33 N 4.85 |
| (4) | xanthenyl | 63.2 | 198–199.5 | 3.85(2H, singlet, —C$\underline{H}$₂—O—) 5.04(1H, singlet, —CO—C$\underline{H}\diagdown$) 6.83–7.40(8H, multiplet, aromatic proton) | 1725($\diagdown$C=O) | C₂₂H₂₄ClNO₃ C 68.47 H 6.27 N 3.63 | C 68.45 H 6.32 N 3.57 |

60

(B) General procedure of 8-(2'-acyloxyethyl)pyrrolizidine

To a stirred solution of one equivalent of 8-(2'-hydroxyethyl)pyrrolizidine in chloroform was added dropwise 1.1 equivalent of acid chloride under ice-cooling and the mixture was stirred for 1 hour at a room temperature. The residue obtained by removal of the solvent was subjected to recrystallization from ethanol-ether to yield the hydrochlorides of the desired products shown in Table 7 below.

TABLE 7

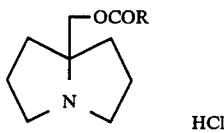
HCl

| Compound No. | R | Yield (%) | m.p. (°C.) | NMR(CDCl₃)δ Free Base | IR$\nu_{max}^{KBr}$cm⁻¹ | Elemental Analysis (%) Calcd. | Found |
|---|---|---|---|---|---|---|---|
| (1) | —CH₃ | 80 | 151–153 | 2.04(3H, singlet, —OCOC$\underline{H}$₃) 2.35(2H, triplet, J=6Hz, —C$\underline{H}$₂—CH₂—O—) 4.18(2H, triplet, J=6Hz, —CH₂—C$\underline{H}$₂—O—) | 1735(>C=O) | C₁₁H₂₀ClNO₂ C 56.52 H 8.63 N 5.99 | C 56.50 H 8.72 N 6.00 |
| (2) | phenyl | 92 | 178–180 | 2.54(2H, triplet, J=6Hz, —C$\underline{H}$₂—CH₂—O—) 4.48(2H, triplet, J=6Hz, —CH₂—C$\underline{H}$₂—O—) | 1730(>C=O) | C₁₆H₂₂ClNO₂ C 64.96 H 7.50 N 4.74 | C 64.97 H 7.51 N 4.76 |
| (3) | 4-methoxyphenyl | 93 | 167–169 | 2.50(2H, triplet, J=6Hz, —C$\underline{H}$₂—CH₂—O—) 3.83(3H, singlet, —OC$\underline{H}$₃) 4.41(2H, triplet, J=6Hz, —CH₂—C$\underline{H}$₂—O—) 6.84(2H, doublet, J=8.5Hz, aromatic H ortho to OMe) 7.84(2H, doublet, J=8.5Hz, aromatic H meta to OMe) | 1705(>C=O) | C₁₇H₂₄ClNO₃ C 62.66 H 7.42 N 4.30 | C 62.66 H 7.45 N 4.30 |
| (4) | xanthenyl | 71.3 | 177.5–178.5 | 4.10(2H, triplet, J=6Hz, —C$\underline{H}$₂—CH₂—O—) 4.96(1H, singlet, —CO—C$\underline{H}$<) 6.87–7.33(8H, multiplet aromatic proton) | 1730(>C=O) | C₂₃H₂₆ClNO₃ C 69.07 H 6.55 N 3.50 | C 68.97 H 6.65 N 3.48 |

EXAMPLE 12

General procedure of 8-substituted hydroxymethyl pyrrolizidine

To one equivalent of 8-hydroxylmethylpyrrolizidine dissolved in benzene was added dropwise a solution of 2 equivalents of methane sulfonylchloride in benzene, and the mixture was stirred for 3 hours at a room temperature. To the mixture was added hexane, and the precipitating oily substance was separated. The oily substance dissolved in dioxane was added dropwise to a sodium alkoxide solution prepared by adding 1.7 equivalent of sodium hydride to 1.5 equivalent of aralkyalcohol dissolved in dioxane followed by reflux for one hour, and the whole mixture was heated under reflux for 2 hours. An excess sodium alkoxide was decomposed with water and the resulting mixture was extracted with 5% hydrochloric acid solution. The aqueous layer was washed with benzene, and basified with a 20% sodium hydroxide solution, which was then subjected to extraction with chloroform. The chloroform layer was washed with a saturated sodium chloride solution, dried over anhydrous magnesium sulfite, and evaporated to give the compounds as an oil as shown in Table 8 below.

TABLE 8

| | 8-methoxymethylpyrrolizidine | 8-benzyloxymethylpyrrolizidine | 8-diphenylmethyloxymethyl-pyrrolizidine |
|---|---|---|---|
| Yield (%) | 45 | 50 | 36.4 |
| m.p. (°C.) | (Oil) | 120–122 (Picrate) | 248–249 (decomp.) (hydrochloride) |
| Elemental Analysis (%) | $C_9H_{17}NO$ (Free base) | $C_{21}H_{24}N_4O_8$ | $C_{21}H_{26}ClNO$ |
| Calcd. | | | |
| C | 69.63 | 54.78 | 73.34 |
| H | 11.04 | 5.25 | 7.62 |
| N | 9.02 | 12.17 | 4.07 |
| Found | | | |
| C | 69.88 | 54.65 | 73.36 |
| H | 11.20 | 5.32 | 7.81 |
| N | 9.17 | 12.08 | 3.78 |
| NMR ($CDCl_3$) | 3.25(3H, singlet, —O—C$\underline{H}_3$) | 3.2(2H, singlet, —C$\underline{H}_2$—O—CH$_2$C$_6$H$_5$) | 3.17(2H, singlet, —C$\underline{H}_2$—O—CH$\langle$) |
| | | 4.51(2H, singlet, —O—C$\underline{H}_2$—C$_6$H$_5$) | 5.32(1H, singlet, —O—C$\underline{H}\langle$) |
| | | 7.26(5H, singlet, —C$_6\underline{H}_5$) | 7.25(10H, singlet, =(C$_6\underline{H}_5$)$_2$) |

(B) General procedure of 8-(2'-substituted hydroxyethyl)pyrrolizidine

To one equivalent of 8-(2'-hydroxyethyl)pyrrolizidine dissolved in benzene was added dropwise a solution of 1.1 equivalent of methane sulfonyl chloride in benzene and the mixture was stirred for 3 hours at a room temperature. To the mixture was added hexane, and the precipitating oil was recrystallized from methanol-ether to give 8-(2'-methanesulfonyloxyethyl)-pyrrolizidine hydrochloride (yield: 35.6%) as colorless crystal, m.p. 103°–106° C. The hydrochloride was added to a sodium alkoxide solution prepared by adding 6 equivalents of sodium hydride to 3 equivalents of aralkyl alcohol dissolved in dioxane under stirring with ice-cooling followed by reflux for 1–2 hours and the mixture was heated under reflux for 3–5 hours. The reaction mixture was cooled, and water was added thereto, followed by extraction with chloroform. The residue obtained by removal of the solvent was dissolved in ether, which was extracted with 10% hydrochloric acid solution. The aqueous layer was basified with 40% sodium hydroxide solution, and extracted with ether. The ether layer was washed with saturated sodium chloride solution, dried over anhydrous magnesium sulfate, and evaporated to give the compounds shown in Table 9 below.

TABLE 9

| | 8-(2'-methoxyethyl)pyrrolizidine | 8-(2'-benzyloxyethyl)pyrrolizidine | 8-{(2'-diphenylmethyl)hydroxyethyl}pyrrolizidine |
|---|---|---|---|
| Yield (%) | 85.1 | 89.8 | 77.9 |
| m.p. (°C.) | 95–96 (Picrate) | 92–94 (Picrate) | 108–109.5 (Picrate) |
| Elemental Analysis (%) | $C_{16}H_{22}N_4O_8$ | $C_{22}H_{26}N_4O_8$ | $C_{28}H_{30}N_4O_8$ |
| Calcd. | | | |
| C | 48.24 | 55.69 | 61.08 |
| H | 5.57 | 5.52 | 5.49 |
| N | 14.07 | 11.81 | 10.18 |
| Found | | | |
| C | 48.18 | 55.78 | 61.07 |
| H | 5.63 | 5.67 | 5.44 |
| N | 14.20 | 11.85 | 10.12 |
| NMRδ ($CDCl_3$) | 3.26(3H, singlet, —O—C$\underline{H}_3$) | (Hydrochloride) | 1.8(2H, triplet, J = 7Hz, —C$\underline{H}_2$—CH$_2$—O—) |
| | | 2.2(2H, triplet, J = 6Hz, —C$\underline{H}_2$—CH$_2$—O—) | 3.5(2H, triplet, J = 7Hz, —CH$_2$—C$\underline{H}_2$—O—) |
| | | 3.6(2H, triplet, J = 6Hz, —CH$_2$—C$\underline{H}_2$—O—) | 5.2(1H, singlet, —O—C$\underline{H}\langle$) |
| | | 4.4(2H, singlet, —C$\underline{H}_2$ ph) | 7.2(10H, broad singlet, =(C$_6\underline{H}_5$)$_2$) |
| | | 7.2(5H, singlet, —C$_6\underline{H}_5$) | |

(C) Preparation of 8-{(2'-diphenylmethyl)hydroxyethyl}pyrrolizidine

A suspension of 2.45 g of benzhydrol and 516 mg. of sodium amide in 50 ml. of anhydrous toluene was refluxed for 24 hours.

On the other hand, 465 mg. of 8-(2'-hydroxyethyl)-pyrrolizidine dissolved in 10 ml. of thionyl chloride was refluxed for 2 hours to yield 8-(2'-chloroethyl)pyrrolizidine hydrochloride as crystals. To the stirred suspension of the sodium salt of the above benzhydrol was added a hydrochloride of chloride and the mixture was refluxed for 2 hours. The reaction solution was treated with water, then the organic layer was separated. The organic layer was extracted with 10% hydrochloric acid solution. The aqueous layer was basified with 40% sodium hydroxide solution, and extracted with chloroform. The chloroform layer was washed with water, dried over anhydrous magnesium sulfate, evaporated to give 433 mg. of pale yellow oil. This substance was subjected to column-chromatography using 40 g. of alumina to give 285 mg (29.6%) of the above-mentioned 8-{(2'-diphenylmethyl)hydroxyethyl)}pyrrolizidine.

EXAMPLE 13

(A) Preparation of 8-aminomethylpyrrolizidine

To a stirred suspension of 5.7 g (0.15 mol.) of lithium aluminium hydride in 150 ml. of anhydrous ether was added dropwise a solution of 6.8 g (0.05 mol.) of 8-cyanopyrrolizidine in 50 ml. of anhydrous ether, and the mixture was refluxed for 2 hours. An excess lithium aluminium hydride was decomposed with 40% sodium hydroxide solution under ice-cooling and the organic layer was separated. This ether layer was washed with saturated sodium chloride solution, dried over anhydrous potassium carbonate, and evaporated off. The residue was subjected to distillation under reduced pressure to yield 5.33 g. (yield: 76%) of 8-aminomethylpyrrolizidine as colorless oil, b.p. 76–77° C. (8 mmHg).

IR $_{max}^{neat}$ cm$^{-1}$: 3350 (—NH$_2$)

NMR(CDCl$_3$)$\delta$: 1.15 (2H, singlet, —CH$_2$—NH$_2$ disappeared by D$_2$O exchange) 2.45 (2H, singlet, —CH$_2$—NH$_2$).

This product was made to its hydrochloride by conventional manner, followed by recrystallization from methanol to yield subliming colorless scales.

Elemental Analysis (%): C$_8$H$_{18}$Cl$_2$N$_2$. Calcd.: C 45.08, H 8.51, N 13.14. Found: C 45.40, H 8.53, N 13.01.

(B) Preparation of 8-(2'-aminoethyl)pyrrolizidine

To a stirred suspension of 10.0 g. of lithium aluminium hydride in 250 ml. of anhydrous ether was added dropwise under ice-cooling 12.5 g. of 8-cyanomethylpyrrolizidine dissolved in 50 ml. of anhydrous ether, followed by stirring at a room temperature for further 2 hours. The reaction mixture was treated as in a manner similar to the Method (A) above, then the residue was subjected to distillation under reduced pressure to yield 10.7 g (yield: 84%) of 8-(2'-aminoethyl)pyrrolizidine as colorless oil, b.p. 87–88° C. (6 mmHg).

NMR(CDCl$_3$)$\delta$: 1.48 (2H, singlet —NH$_2$, disappeared by D$_2$O exchange).

This product was converted to the corresponding hydrochloride, which was recrystallized from ethanol to give colorless crystals subliming at a temperature not lower than 200° C.

Elemental Analysis (%): C$_9$H$_{20}$Cl$_2$N$_2$·½H$_2$O. Calcd.: C 45.77, H 8.96, N 11.86. Found: C 45.84, H 9.17, N 11.65.

(A) Preparation of 8-(N,N-dimethylaminomethyl)pyrrolizidine

To a stirred solution of 1.4 g. of 8-aminomethylpyrrolizidine in 2.8 g of 90% formic acid was added dropwise under ice-cooling 1.9 g of a 35% aqueous solution of formalin. The mixture was heated under reflux for 5 hours, which was then basified with a 10% sodium hydroxide solution, followed by extraction with chloroform. This chloroform layer was washed with saturated sodium chloride solution, dried over anhydrous magnesium sulfate, followed by removal of the solvent by evaporation to yield 0.8 g (yield: 47.6%) of 8-(N,N-dimethylaminomethyl)pyrrolizidine.

NMR(CDCl$_3$)$\delta$: 2.23 (2H, singlet, —CH$_2$—N<) 2.30 (6H, singlet, —N(CH$_3$)$_2$).

This product was converted to the corresponding picrate by conventional manner, which was recrystallized from acetone-ether to yield yellow crystals decomposing at 206–209° C.

Elemental Analysis (%): C$_{22}$H$_{26}$N$_8$O$_{14}$. Calcd.: C 42.17, H 4.18, N 17.89. Found: C 42.09, H 4.15, N 17.83.

(B) Preparation of 8-2'-(N,N-dimethyl)aminoethyl pyrrolizidine

To 0.77 g of 8-(2-aminoethyl)pyrrolidine dissolved in 1.28 g of 90% formic acid was added 0.94 g. of a 35% aqueous solution of formalin, which was heated under reflux for 3 hours. After removal of the solvent, the resulting mixture was basified with 10% sodium hydroxide solution, followed by extraction with chloroform. Removal of the solvent by evaporation gave quantitatively 0.91 g of 8-{22'-(N,N-dimethyl)aminoethyl}pyrrolizidine as an oil.

NMR(CDCl$_3$)$\delta$: 2.2 (6H, singlet, —N(CH$_3$)$_2$).

The picrate of this product was of yellow crystals, m.p. 200°–205° C.

Elemental Analysis (%): C$_{23}$H$_{28}$N$_8$O$_{14}$. Calcd.: C 43.13, H 4.41, N 17.50. Found: C 43.14, H 4.41, N 17.32.

(C) Preparation of 8-(N-benzylaminoethyl)pyrrolizidine

To a solution of 1.4 g. of 8-aminoethylpyrrolizidine in 30 ml. of benzene was added dropwise 1.12 g. of benzaldehyde. The mixture was heated under reflux for 2 hours, then the solvent was evaporated. The residue was dissolved in ethanol, to which was gradually added 0.5 g. of sodium borohydride with stirring under ice-cooling, then the mixture was heated for 30 minutes under reflux. The solvent was removed by evaporation, and the residue was treated with water, then the aqueous solution was subjected to extraction with chloroform. The chloroform layer was washed with saturated sodium chloride solution, dried over anhydrous magnesium sulfate and evaporated to give 2.3 g. of 8-(N-benzylaminomethyl)pyrrolizidine quantitatively as a colorless oil.

NMR(CDCl$_3$): 2.47 (2H, singlet, —CH$_2$—NH—). 3.79 (2H, singlet, —CH$_2$—C$_6$H$_5$). 7.26 (5H, singlet, —C$_6$H$_5$).

The picrate of this product was recrystallized from methanol-ether to yield yellow crystals, m.p. 140°–141° C.

Elemental Analysis (%): C$_{21}$H$_{25}$N$_5$O$_7$. Calcd.: C 54.89, H 5.48, N 15.24. Found: C 54.88, H 5.49, N 15.21.

(D) Preparation of 8-(N-benzyl-N-methyl)aminomethylpyrrolizidine

A solution of 0.46 g of 8-(N-benzylaminomethyl) pyrrolizidine and 0.3 g. of paraformaldehyde in 30 ml. of ethanol was heated under reflux for 30 minutes. To the stirred solution was slowly added under ice-cooling 0.19 g. of sodium borohydride and stirring was continued for 2 hours, followed by removal of the solvent by evaporation. The residue was treated with water and extracted with chloroform. The chloroform layer was washed with saturated sodium chloride solution, dried over anhydrous magnesium sulfate, and evaporated to leave 0.47 g. of 8-(N-benzyl-N-methyl)aminomethylpyrrolizidine as a colorless oil. Yield 96.3%.

NMR(CDCl$_3$)δ: 2.25 (3H, singlet, >N—CH$_3$). 2.38 (2H, singlet, —CH$_2$—N<). 3.57 (2H, singlet, —CH$_2$—C$_6$H$_5$).

The picrate of this product gave yellow crystals m.p. 183°–185° C.

Elemental Analysis (%): C$_{28}$H$_{30}$N$_8$O$_{14}$. Calcd.: C 47.86, H 4.30, N 15.95. Found: C 47.57, H 4.28, N 15.89.

(E) Preparation of 8-{2'-(N-benzyl)aminoethyl}pyrrolizidine

A solution of 770 mg. of 8-(2'-aminoethyl)pyrrolizidine and 540 mg. of benzaldehyde in 100 ml. of benzene was heated under reflux for 1 hour. The solvent was removed by evaporation, and the residue was dissolved in 50 ml. of metanol. To the stirred solution wa added gradually 500 mg. of sodium borohydride. The mixture was stirred for 1 hour at a room temperature, and evaporated to leave an oil which was extracted with benzene. The extract was washed with saturated sodium chloride solution, dried over anhydrous magnesium sulfate, and evaporated to leave 1.107 g. (yield: 64.4%) of 8-{2'-(N-benzyl)aminoethyl}pyrrolizidine as an oil.

NMR(CDCl$_3$)δ: 3.77 (2H, singlet, >N—CH$_2$—ph). 7.30 (5H, singlet, —C$_6$H$_5$).

This product was converted to its picrate by conventional manner, which was recystallized from acetone-ether to yield yellow needles, m.p. 127.5°–128° C.

Elemental Analysis (%): C$_{22}$H$_{27}$N$_5$O$_7$. Calcd.: C 55.80, H 5.75, N 14.79. Found: C 55.78, H 5.80, N 14.68.

(F) Preparation of 8-guanidinomethylpyrrolizine

A mixture of 0.56 g. of 8-aminomethylpyrrolizidine and 0.843 g. of S-methylisourea sulfate in 50 ml. of ethanol was heated under reflux for 5 hours. After cooling the reaction mixture, the resulting precipitates were collected by filtration and recrystallized from water-ethanol to yield 0.94 g. (yield: 97.5%) of 8-guanidinomethylpyrrolizidine sulfate as colorless crystals, m.p. 270° C.

Elemental Analysis (%): C$_9$H$_{20}$N$_4$O$_4$S.H$_2$O. Calcd.: C 36.23, H 7.43, N 18.78. Found: C 36.21, H 7.51, N 18.64.

(G) Preparation of 8-(2'-guanidinoethyl)pyrrolizidine:

Treatment of 0.45 g. of 8-(2'-aminoethyl)pyrrolizidine as in a manner similar to the Method (F) gave 0.58 g (yield: 78%) of 8-(2'-guanidinoethyl)pyrrolizidine sulfate as colorless crystals, m.p. 270° C.

Elemental Analysis (%): C$_{10}$H$_{22}$N$_4$O$_4$S. Calcd.: C 40.80, H 7.53, N 19.03. Found: C 40.89, H 7.61, N 19.08.

EXAMPLE 15

(A) General procedure of 8-acylaminomethylpyrrolizidine

A mixture of 1 equivalent of 8-aminomethylpyrrolizidine and 1 equivalent of acid chloride was stirred at a room temperature for 20–24 hours. The precipitating crystals were recrystallized from isopropylalcohol-ether to yield compounds shown in Table 10 below.

TABLE 10

|  | 8-(N—acetyl)aminomethylpyrrolizidine hydrochloride | 8-(N—benzoyl)aminomethylpyrrolizidine hydrochloride |
|---|---|---|
| Yield (%) | 75 | 88.1 |
| m.p. (°C.) | Hygroscopic | 137.5–139 |
| Elemental Analysis (%) | C$_{10}$H$_{18}$N$_2$O (free base) | C$_{15}$H$_{21}$ClN$_2$O |
| Calcd. | | |
| C | 65.89 | 64.16 |
| H | 9.96 | 7.54 |
| N | 15.37 | 9.98 |
| Found | | |
| C | 65.98 | 64.18 |
| H | 10.07 | 7.60 |
| N | 15.21 | 9.82 |
| IR$\nu_{max}$cm$^{-1}$ | (Nujol) | (KBr) |
|  | 3225(—NH—) | 3425(—NH—) |
|  | 1665(>C=O) | 1645(>C=O) |
| NMR (CDCL$_3$) | 3167(2H, doublet, J = 6.0Hz, —CH$_2$—NH—) | 3.92(2H, doublet, J = 6.4Hz, —CH$_2$—NH—) |
| Free base | 8.24–8.82(1H, broad singlet, —NH—) |  |
|  |  | 7.27–7.68(3H, multiplet, 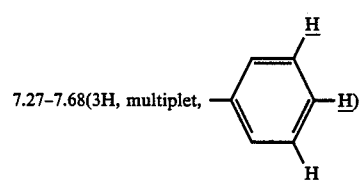) |
|  |  | 7.86–8.30(2H, multiplet, 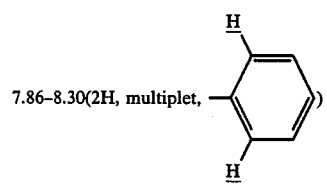) |

TABLE 10-continued

| 8-(N—acetyl)aminomethylpyrrolizidine hydrochloride | 8-(N—benzoyl)aminomethylpyrrolizidine hydrochloride |
|---|---|
| | 8.88–9.38(1H, triplet, J = 6.4Hz, —CH$_2$—N$\underline{H}$—) |

(B) General procedure of 8-{2'-(N-acyl)aminoethyl}pyrrolizidine (i) To one equivalent of 8-(2'-aminoethyl)pyrrolizidine dissolved in benzene was added a solution of 1.1 equivalent of acid chloride in benzene. The mixture was stirred for 2–5 hours at room temperature, followed by addition of hexane. Recrystallization of precipitating crystals from ethanol-ether or iso-propanol-ether gave hydrochlorides of the compounds (1) and (4) shown in the Table 11 below.

(ii) To a stirred solution of one equivalent of 8-(2'-aminoethyl)pyrrolizidine in chloroform was added 1.1 equivalent of acid chloride under ice-cooling. The mixture was stirred for 2 hours at room temperature. The residue obtained by removal of the solvent was purified by means of column-chromatography. The products thus obtained were converted to the corresponding hydrochlorides of compounds (2) and (3) shown in tha Table 11.

TABLE 11a

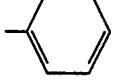

| Compound No. | R | Yield (%) | m.p. (°C.) (hydrochloride) | NMR (CDCl$_3$)δ | IR$\nu_{max}$cm$^{-1}$ |
|---|---|---|---|---|---|
| (1) | —CH$_3$ | 78.9 | 137–139 | 2.0(3H, singlet, —CO—C$\underline{H}_3$) | 1660 (—NHCO—) |
| (2) | 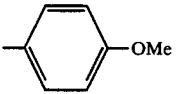 | 60 | oil | 7.0–8.0(5H, multiplet, 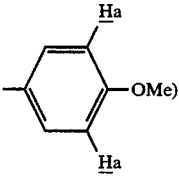) | 1640 (—NHCO—) |
| (3) | 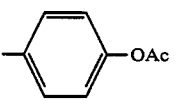—OMe | 69.5 | 155–157 | 3.8(3H, singlet, —OC$\underline{H}_3$) 6.8(2H, doublet, J=8Hz, H$\underline{a}$, H$\underline{a}$, —OMe) 7.7(2H, doublet, J=8Hz, H$\underline{b}$, H$\underline{b}$, —OMe) | 1643 (—NHCO—) |
| (4) | 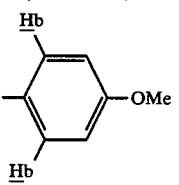—OAc | 84.7 | 205–208 | 2.3(3H, singlet, —CO—C$\underline{H}_3$) | 1760 (—O—CO—) |

TABLE 11a-continued

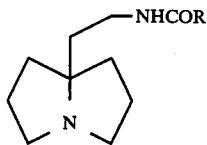

| Compound No. | R | Yield (%) | m.p. (°C.) (hydrochloride) | NMR (CDCl₃)δ | IR$\nu_{max}$cm$^{-1}$ |
|---|---|---|---|---|---|
| | | | | 7.1(2H, doublet, J=8Hz, Ha [aromatic ring with OAc, Ha positions]) | 1658 (—NHCO—) |
| | | | | 8.1(2H, doublet, J=8Hz, Hb [aromatic ring with OAc, Hb positions]) | |

TABLE 11b

| Compound No. | Molecular Formula | Elemental Analysis (%) Calcd. | | Found | |
|---|---|---|---|---|---|
| (1) | C₁₁H₂₁ClN₂O | C | 56.76 | C | 56.88 |
| | | H | 9.09 | H | 9.25 |
| | | N | 12.04 | N | 12.16 |
| (2) | C₁₆H₂₃ClN₂O | C | 65.18 | C | 65.05 |
| | | H | 7.86 | H | 7.99 |
| | | N | 9.50 | N | 9.33 |
| (3) | C₁₇H₂₅ClN₂O₂ | C | 62.85 | C | 62.92 |
| | | H | 7.76 | H | 7.80 |
| | | N | 8.62 | N | 8.60 |
| (4) | C₁₈H₂₅ClN₂O₃ | C | 61.27 | C | 61.38 |
| | | H | 7.14 | H | 7.40 |
| | | N | 7.94 | N | 7.77 |

EXAMPLE 16

General procedure of 8-(4'-substituted benzoylaminomethyl)pyrrolizidine (A) Fusion with esters A mixture of one equivalent of 8-aminomethylpyrrolizidine and 1 equivalent of ethyl-4'-substituted benzoate was subjected to fusion reaction. The resultant was recrystallized from a suitable solvent or purified by recrystallization of its hydrochloride as shown in the Table 12 below.

TABLE 12

| Compound | 8-(4'-methoxybenzoylaminomethyl)pyrrolizidinehydrochloride | 8-(4'-aminobenzoylaminomethyl)pyrrolizidine | 8-(4'-hydroxybenzoylaminomethyl)pyrrolizidine |
|---|---|---|---|
| Reaction Temp. (°C.) | 120–160 | 120–175 | 120 |
| Reaction Time | 12 | 12 | 2 |
| Yield (%) | 80.3 | 52.9 | 72.9 |
| m.p. (°C.) | 148.5–150 | 201–204.5 | 260–262.5 (sublimation) |
| Recrystallization Solvent | methanol | ethanol-hexane | methanol |
| IR$_{max}$cm$^{-1}$ | (Nujol) 3330 (—NH—) 1620 (>C=O) | (Nujol) 3320 (—NH—) 3155 (—NH—) 1628 (>C=O) | (KBr) 3305 (—NH—) 1640 (>C=O) |
| NMRδ | (CDCl₃—CD₃OD) 3.75(2H, singlet, —CH₃) | (CD₃OD—CD₃COCD₃) 3.36(2H, singlet, —CH₂—NH—) | (CDCl₃—CD₃OD) 3.40(2H, singlet, —CH₂—NH—) |

TABLE 12-continued

| Compound | 8-(4'-methoxybenzoylaminomethyl)pyrrolizidinehydrochloride | 8-(4'-aminobenzoylaminomethyl)pyrrolizidine | 8-(4'-hydroxybenzoyl-aminomethyl)pyrrolizidine |
|---|---|---|---|
| | 3.85(3H, singlet, —O—CH$_3$) 6.98(2H, doublet, J=9.0Hz, —C$_6$H$_4$—OMe) | 6.63(2H, doublet, J=8.4Hz, —CO—C$_6$H$_4$—NH$_2$) | 6.89(2H, doublet, J=8.4Hz, —C$_6$H$_4$—OH) |
| | 7.92(2H, doublet, J=9.0Hz, —C$_6$H$_4$—OMe) | 7.61(2H, doublet, J=8.4Hz, —CO—C$_6$H$_4$—NH$_2$) | 7.18(2H, doublet, J=8.4Hz, —C$_6$H$_4$—OH) |
| Elemental Analysis (%) Calcd. | C$_{16}$H$_{24}$(lN$_2$O$_2$·0.5H$_2$O) | C$_{15}$H$_{21}$N$_3$O | C$_{15}$H$_{20}$N$_2$O$_2$ |
| C | 60.08 | 69.46 | 69.20 |
| H | 7.56 | 8.16 | 7.74 |
| N | 8.76 | 16.21 | 10.76 |
| Found | | | |
| C | 60.26 | 69.53 | 69.20 |
| H | 7.47 | 8.23 | 7.78 |
| N | 8.73 | 16.16 | 10.75 |

(B) Fusion with carboxylic acids

A mixture of one equivalent of 8-aminomethylpyrrolizidine and one equivalent of 4-substituted benzoic acid was subjected to fusion reaction. The resultant was purified as in a manner similar to the method (A) to give the compounds shown in the Table 13 below.

TABLE 13

| Compound Name | 8-4'-methoxybenzoylaminomethyl)pyrrolizidine | 8-(4'-aminobenzoylaminomethyl)pyrrolizidine | 8-(4'-hydroxybenzoylaminomethyl)pyrrolizidine |
|---|---|---|---|
| Reaction temp. (°C.) | 175 | 185 | 175 |
| Reaction time | 2 | 12 | 5 |
| Yield (%) | 55 | 80.3 | resinification |

TABLE 13-continued

| Compound Name | 8-4'-methoxybenzoylaminomethyl)pyrrolizidine | 8-(4'-aminobenzoylaminomethyl)pyrrolizidine | 8-(4'-hydroxybenzoylaminomethyl)pyrrolizidine |
|---|---|---|---|
| | | | by decomposition |

EXAMPLE 17

(A) General procedure of {8--(2'-pyridinyl)-N-acyl}aminomethylpyrrolizidine

A solution of one equivalent of 8-N-(2'-pyridinyl-)aminomethylpyrrolizidine and 1 equivalent of acid chloride in benzene were stirred for 28 hours at a room temperature. The precipitating crystals were recrystallized from isopropylalcohol-ether to yield the compounds shown in the Table 14 below.

TABLE 14

| | 8-N—(2'-pyrridinyl)-N—acetyl aminomethylpyrrolizidine hydrochloride | 8-{N—(2'-pyrridinyl)-N—benzoyl} aminomethylpyrrolizidine hydrochloride |
|---|---|---|
| Yield (%) | 75.7 | 90 |
| m.p. (°C.) | Hygroscopic | 167.5–170.5 |
| Elemental Analysis (%) | C$_{15}$H$_{21}$N$_3$O (Free base) | C$_{20}$H$_{24}$ClN$_3$O |
| Calcd. | | |
| C | 69.46 | 67.12 |
| H | 8.16 | 6.76 |
| N | 16.21 | 11.74 |
| Found | | |
| C | 69.08 | 67.18 |
| H | 8.34 | 6.87 |
| N | 16.17 | 11.65 |
| IR$_{max}^{KBr}$cm$^{-1}$ | 1645(>C=O) | 1660(>C=O) |

TABLE 14-continued

| | 8-N—(2'-pyrridinyl)-N—acetyl aminomethylpyrrolizidine hydrochloride | 8-{N—(2'-pyrridinyl)-N—benzoyl} aminomethylpyrrolizidine hydrochloride |
|---|---|---|
| NMRδ(CDCl$_3$) Free base | 2.02(3H, singlet, —CO—C$\underline{H}_3$) | 4.60(2H, singlet, —C$\underline{H}_2$—N<) <br><br> 8.70(1H, multiplet, 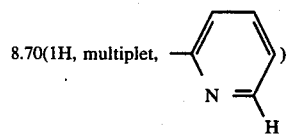) |

(B) Method of preparing 8-{2'-(N-benzoyl)anilinoethyl}pyrrolizidine

To a stirred suspension of 0.61 g. of 8-(2-anilinoethyl)pyrrolizidine hydrochloride, 20 ml. of 10% sodium hydroxide solution, and 30 ml. of chloroform was added dropwise 0.62 g of benzoyl chloride under ice-cooling and stirring was continued for 1 hour. The chloroform layer was separated, and the solvent was evaporated. The residue was dissolved in 5% hydrochloric acid solution, and washed with ether. The aqueous layer was basified with 28% ammonia solution of, and extracted with chloroform. The chloroform layer was washed with saturated sodium chloride solution, dried over anhydrous magnesium sulfate, and evaporated to yield quantitatively 0.67 g of 8-{2'-(N-benzoyl)anilinoethyl} pyrrolizidine as an oil.

IR $_{max}^{CHCl_3}$ cm$^{-1}$: 1630 (—CON ).

NMR(CDCl$_3$)δ: 3.8–4.1 (2H, multiplet, —C$\underline{H}_2$—N<). 7.0–7.3 (10H, multiplet, —C$_6$$\underline{H}_5$, —C$\underline{H}_2$—C$_6$H$_5$).

This product was converted to corresponding picrate as usual manner, which was recrystallized from acetone-ether to yield yellow crystals, m.p. 185°–186.5° C.

Elemental Analysis (%): C$_{28}$H$_{29}$N$_5$O$_8$. Calcd.: C 59.67, H 5.19, N 12.43. Found: C 59.25, H 5.19, N 12.28.

EXAMPLE 18

Method of preparing 8-2'-(N- benzyl)anilinoethyl pyrrolizine

To a stirred suspension of 0.28 g. of lithium aluminium hydride in 50 ml. of anhydrous ether was added dropwise 0.61 g. of 8-{2'-(N-benz yl)anilinoethyl}pyrrolizidine. The mixture was heated under reflux for 5 hours. To the stirred reaction mixture was added under ice-cooling an aqueous solution of sodium hydroxide to decompose an excess lithium aluminium hydride, followed by separation of the organic layer. The organic layer was washed with saturated sodium chloride solution, dried over anhydrous magnesium sulfate, and evaporated to leave 0.42 g. of oil, which was subjected column-chromatography using 42 g. of alumina. The eluate of the solvent system chloroform: benzene=1:1, gave 0.28 g. (yield: 48.3%) of 8-{2'-(N-benzyl)-anilinoethyl}pyrrolizine as an oil.

NMR(CDCl$_3$)δ: 4.50 (2H, singlet, N—C$\underline{H}_2$—C$_6$H$_5$). 6.5–7.25 (10H, multiplet, —C$_6$$\underline{H}_5$, —C$\underline{H}_2$—C$_6$H$_5$).

This product was converted to corresponding picrate by a conventional manner, which was recrystallized from acetone-ether to yield yellow crystals, m.p. 145°–148.5° C.

Elemental Analysis (%): C$_{34}$H$_{34}$N$_8$O$_{14}$. Calcd.: C 52.42, H 4.40, N 14.39. Found: C 52.44, H 4.42, N 14.15.

EXAMPLE 19

(A) Preparation of 8-(N-methyl)aminomethylpyrrolizidine:

To a stirred suspension of 0.42 g. of 8-aminomethyl-pyrrolizidine, 15 ml. of a 10% sodium hydroxide solution, and 15 ml. of chloroform was added under ice-cooling 0.326 g. of ethyl chloroformate, and the mixture was stirred for 3 hours at a room temperature. The chloroform layer was separated, which was washed with saturated sodium chloride solution, dried over anhydrous magnesium sulfate, and evaporated to yield 0.63 g. of colorless oil. The colorless oily substance was added, under ice-cooling, to a stirred suspension of 0.42 g of lithium aluminium hydride in 50 ml. of anhydrous ether, followed by stirring under reflux for 1.5 hour. After cooling the mixture, a 20% sodium hydroxide solution was added thereto to decompose an excess of the lithium aluminium hydride, followed by separation of the organic layer. The organic layer was washed with saturated sodium chloride solution dried over anhydrous magnesium sulfate, and evaporated to leave 0.31 g (yield: 67.1%) of 8-(N-methyl)aminomethylpyrrolizidine.

NMR(CDCl$_3$): 2.44 (3H, singlet, —NH—C$\underline{H}_3$).

This product was converted to corresponding picrate as yellow crystals deconposing at 211°–266° C.

Elemental Analysis (%): C$_{21}$H$_{24}$N$_8$O$_{14}$. Calcd.: C 41.18, H 3.95, N 18.30. Found: C 41.31, H 4.04, N 18.18.

(B) Preparation of 8-{2'-(N-methyl)aminoethyl}pyrrolizidine

Treatment of 0.462 g. of 8-(2-aminoethyl)pyrrolizidine as in a manner similar to the method (A) above gave 0.29 g. (yield: 57.5%) of 8-{2'-(N-methyl)aminoethyl}pyrrolizidine as an oil.

NMR(CDCl$_3$)δ: 2.42 (3H, singlet, —NH—C$\underline{H}_3$).

This product was converted to corresponding picrate, which was recrystallized from acetone-ether to yield yellow needles, m.p. 187°–190° C.

Elemental Analysis (%): C$_{22}$H$_{26}$N$_8$O$_{14}$. Calcd: C 42.17, H 4.18, N 17.89. Found: C 42.44, H 4.34, N 17.61.

EXAMPLE 20

(A) General procedure of 8-(N-substituted)aminomethylpyrrolizidine

To a stirred suspension of 2 equivalents of lithium aluminium hydride in anhydrous ether was added gradually at a room temperature 1 equivalent of 8-(N-substituted)aminocarbonylpyrolizidine, and the mixture was stirred for 2 hours at room temperature, followed by heating under reflux for 5 hours. An excess lithium aluminium hydride was decomposed with a 20% sodium hydroxide solution, and the ether layer was separated. The ether layer was washed with saturated sodium chloride solution dried over anhydrous potassium carbonate, evaporated to yield the compounds shown in the Table 15 below.

EXAMPLE 21

(A) One gram of 8-substituted pyrrolizidine was dissolved in 10 ml. of methanol. To the solution was added a large excess of alkyl halide, and the mixture was heated under reflux for 15 hours. After removal of the solvent, the resultant was washed with ether, then recrystallized from methanol-ether to yield the

TABLE 15

|  | 8-(N—2'-pyridinyl) aminomethylpyrrolizidine | 8-(N—benzyl-N—phenyl) aminomethylpyrrolizidine | 8-N—benzyl-N—(4'-methoxyphenyl) aminomethylpyrrolizidine |
|---|---|---|---|
| Yield (%) | 90% | 46.5 | 61.3 |
| m.p. (°C.) (Hydrochloride) | 185 | 182–184.5 | 96 |
| Elemental Analysis (%) Calcd. |  |  |  |
|  | $C_{13}H_{21}Cl_2N_3$ | $C_{21}H_{27}ClN_2 \cdot H_2O$ | $C_{22}H_{30}Cl_2N_2O \cdot \frac{1}{2}H_2O$ |
| C | 53.79 | 69.88 | 63.15 |
| H | 7.29 | 8.10 | 7.47 |
| N | 14.48 | 7.76 | 6.70 |
| Found |  |  |  |
| C | 53.67 | 70.21 | 63.02 |
| H | 7.37 | 7.94 | 7.73 |
| N | 14.36 | 7.72 | 6.46 |
| $IR_{max}^{neat}cm^{-1}$ | 3350(—NH—) |  |  |
| NMR$\delta$ (CDCl$_3$) | 3.20(2H, doublet, —C$\underline{H}_2$—NH—) | 3.42(2H, singlet, —C$\underline{H}_2$—N$\langle$) | 3.33(2H, singlet, —C$\underline{H}_2$—N$\langle$) |
|  | 5.00(1H, broad singlet, —NH) | 4.87(2H, singlet, N—C$\underline{H}_2$—ph) | 3.67(3H, singlet, —OC$\underline{H}_3$) |
|  |  | 7.16(5H, singlet, —CH$_2$—C$_6\underline{H}_5$) | 4.71(2H, singlet, —C$\underline{H}_2$—C$_6$H$_5$) |
|  |  | 7.51–8.39(5H, multiplet, —N—C$_6\underline{H}_5$) | 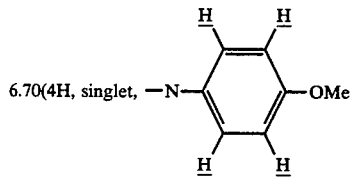 6.70(4H, singlet) |
|  |  |  | 7.17(5H, singlet, —CH$_2$—C$_6\underline{H}_5$) |

(B) Preparation 8-(2'-anilinoethyl)pyrrolizidine

To a stirred suspension of 0.53 g. of lithium aluminium hydride in 70 ml. of anhydrous tetrahydrofuran was added dropwise 1.71 g. of 8-anilinocabonylmethylpyrrolizidine under ice-cooling, then the reaction mixture was heated under reflux for 1 hour, to which was added 10% sodium hydroxide solution to decompose an excess lithium aluminium hydride, followed by separation of the organic layer. The organic layer was washed with saturated sodium chloride solution, dried over anhydrous magnesium sulfate, and evaporated to yield 1.47 g (yield: 91.3%) of 8-(2'-anilinoethyl)pyrrolizidine.

NNR(CDCl$_3$)$\delta$: 6.5–7.3 (5H, multiplet, —C$_6\underline{H}_5$).

This product was converted to corresponding hydrochloride, which was recrystallized from methanol-ether to give colorless needles decomposing at 229° C.

Elemental Analysis (%): $C_{15}H_{24}Cl_2N_2$. Calcd.: C 59.40, H 7.98, N 9.24. Found: C 59.40, H 7.98, N 9.21.

compound (1) and (2) shown in the Table 16 below, respectively.

(B) One gram of 8-substituted pyrrolizidine was dissolved in 10 ml. of sulforane. To the solution was added alkyl halide, which was stirred for 3–20 hours at a room temperature. To the mixture was added a large excess of ether, and the resulting precipitates were recrystallized from ethanol-ether to yield the compounds (3)–(6) and (12) shown in the Table 16 below.

(C) One equivalent of 8-substituted pyrrolizidine was dissolved in an appropriate volume of sulforane. To the solution was added 3–4 equivalents of 4-phenylphenasyl bromide dissolved in acetone, and the mixture was stirred for 18 hours at a room temperature. When crystals precipitated out, the precipitates are collected by filtration as they are. When crystals did not precipitate, ether was added to the reaction solution to cause crystallization, then the object compounds were collected by filtration, followed by recrystallization from ethanol-ether to yield the compounds (8)–(11) shown in the Table 16 below.

TABLE 16a

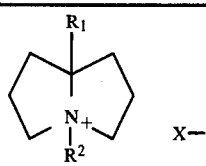

| Compound No. | R¹ | R² | X | Yield (%) | m.p. (°C.) |
|---|---|---|---|---|---|
| (1) | phCH$_2$ | Me | I | 91.8 | >280 |
| (2) | phCH$_2$ | Et | I | 88.3 | 256–258 |
| (3) | phCH$_2$ | BrCH$_2$CH$_2$CH$_2$CH$_2$ | Br | 74.8 | 222–224 |
| (4) | phCH$_2$CH$_2$ | BrCH$_2$CH$_2$CH$_2$CH$_2$ | Br | 50 | 157–159 |
| (5) | phCH$_2$CH$_2$CH$_2$ | BrCH$_2$CH$_2$CH$_2$CH$_2$ | Br | 53 | 192–194 |
| (6) | CH=CHCH$_2$ | BrCH$_2$CH$_2$CH$_2$CH$_2$ | Br | 72.8 | 164 |
| (7) | ph | CH$_2$CO—⟨C$_6$H$_4$⟩—ph | Br | 54 | 212.4–214 |
| (8) | phCH$_2$ | CH$_2$CO—⟨C$_6$H$_4$⟩—ph | Br | 81.4 | 233.5–234.5 |
| (9) | phCH$_2$CH$_2$ | CH$_2$CO—⟨C$_6$H$_4$⟩—ph | Br | 63 | 229–230 (decomp.) |
| (10) | phCH$_2$CH$_2$CH$_2$ | CH$_2$CO—⟨C$_6$H$_4$⟩—ph | Br | 65 | 211–212 (decomp.) |
| (11) | CH=CHCH$_2$ | CH$_2$CO—⟨C$_6$H$_4$⟩—ph | Br | 65.7 | 207–208.5 |
| (12) | phCH$_2$ | phCH$_2$ | Cl | 76.3 | >260 |

TABLE 16b

| Compound No. | Molecular Formula | Elemental Analysis (%) Calcd. | Found |
|---|---|---|---|
| (1) | C$_{15}$H$_{22}$IN | C 52.48  H 6.46  N 4.08 | C 52.45  H 6.44  N 4.05 |
| (2) | C$_{16}$H$_{24}$IN | C 53.78  H 6.77  N 3.92 | C 53.79  H 6.75  N 3.90 |
| (3) | C$_{18}$H$_{27}$Br$_2$N | C 51.81  H 6.52  N 3.36 | C 51.81  H 6.52  N 3.36 |
| (4) | C$_{19}$H$_{29}$Br$_2$N | C 52.92  H 6.78  N 3.25 | C 52.75  H 6.80  N 3.25 |
| (5) | C$_{20}$H$_{31}$Br$_2$N | C 53.95  H 7.02  N 3.15 | C 53.87  H 7.02  N 2.96 |
| (6) | C$_{14}$H$_{25}$Br$_2$N | C 45.79  H 6.86  N 3.82 | C 45.78  H 6.85  N 3.81 |
| (7) | C$_{27}$H$_{28}$BrNO | C 70.12  H 6.10  N 3.03 | C 69.96  H 6.16  N 3.00 |
| (8) | C$_{28}$H$_{30}$BrNO | C 70.58  H 6.35  N 2.94 | C 70.34  H 6.32  N 2.92 |
| (9) | C$_{29}$H$_{32}$BrNO | C 71.01  H 6.58  N 2.86 | C 70.88  H 6.62  N 2.96 |
| (10) | C$_{30}$H$_{34}$BrNO | C 71.42  H 6.79  N 2.78 | C 71.04  H 6.82  N 2.73 |
| (11) | C$_{24}$H$_{28}$BrNO | C 67.60  H 6.62  N 3.29 | C 67.28  H 6.63  N 3.23 |
| (12) | C$_{21}$H$_{26}$ClN | C 76.92  H 7.99  N 4.27 | C 76.89  H 7.98  N 4.23 |

We claim:

1. An 8-substituted pyrrolizidine and a quaternary ammonium salt thereof of the formula:

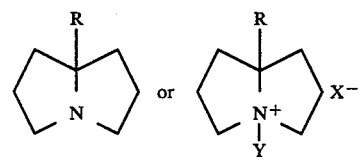

wherein R is an alkyl group containing C$_4$–C$_{10}$ atoms, aralkyl or aryl group containing up to C$_{10}$ atoms; a lower alkoxycarbonyl or a lower alkoxycarbonylmethyl group; a lower alkyl carboxyl group amidated with pyridinylamine, aniline, cyclohexylamine, phenylbenzylamine or methoxyphenylbenzylamine; a lower hydroxyalkyl group which has one or two phenyl, a trihalomethylphenyl or a halophenyl group; a lower alkyl group which has a hydroxyl group esterified with acetic, benzoic, cinnamic, xanthene-carboxylic or methoxybenzoic acid, or etherified with a $C_2$–$C_{13}$ alcohol; a lower alkyl group having a lower alkylamino, guanidino, benzylamino, hydroxybenzylamino, methoxybenzylamino, aminobenzylamino, acetamino, benzoylamino, hydroxybenzoylamino, methoxybenzoylamino, pyridinylamino, aminobenzoylamino, N,N-dimethylamino, 2-(N,N-dimethylamino), N-methyl-N-benzylamino, N-benzyl-N-methoxy-phenylamino, N-benzyl-N-phenylamino, 2-(N-benzoyl-N-phenylamino), N-(2'-pyridinyl)-N-acetylamino or N-(2'-pyridinyl)-N-benzoylamino group; or a lower alkyl group bearing benzoyl, methoxybenzoyl, methylbenzoyl, halobenzoyl or trifluoromethylbenzoyl group; Y stands for a group quaternizing the nitrogen of the pyrrolizidine nucleus, and which is lower alkyl, phenacyl, phenyl-substituted phenacyl, or lower alkyl substituted with halogen, phenyl, phenacyl or phenylphenacyl group and X stands for halogen.

2. A compound according to claim 1 wherein R is a pyridinyl aminocarbonyl, N-benzyl-N-phenylaminocarbonyl, N-benzyl-N-(4'-methoxyphenyl) aminocarbonyl, cyclohexylaminocarbonyl or anilinocarbonylmethyl group.

3. A compound according to claim 1 wherein R is a 2-hydroxy-2-phenylethyl, diphenylhydroxymethyl, 2,2-diphenyl-2-hydroxyethyl, bis(3-chlorophenyl)hydroxymethyl, bis(3-trifluoromethylphenyl)hydroxymethyl, 2-bis(3'-chlorophenyl)hydroxyethyl or 2-bis(3'-trichloromethylphenyl)hydroxyethyl group.

4. A compound according to claim 1 wherein R is an acetoxymethyl, benzyloxymethyl, cinnamoyloxymethyl, xanthene-9-carboxymethyl, 2-benzoyloxyethyl, 2-(4'-methoxybenzoyl)oxyethyl, 2-acetoxyethyl, 2-(xanthene-9'-carboxy)ethyl, methoxymethyl, 2-methoxyethyl, 2-benzyloxyethyl, diphenylmethyloxymethyl or 2-diphenylmethyloxyethyl group.

5. A compound according to claim 1 wherein R is methylaminomethyl, guanidinomethyl, 2-guanidinoethyl, benzylaminomethyl, 2-benzylaminoethyl, hydroxybenzylaminomethyl, methoxybenzylaminomethyl, aminobenzylaminomethyl, pyridinylamino-methyl, acetaminomethyl, 2-acetaminoethyl, benzoylaminomethyl, hydroxybenzoylaminomethyl, methoxybenzoylaminomethyl, aminobenzoylaminomethyl, N,N-dimethylaminomethyl, 2-(N,N-dimethyl-amino)ethyl, N-methyl-N-benzylaminomethyl, N-benzyl-N-methoxyphenylaminomethyl, N-benzyl-N-phenylaminoethyl, 2-(N-benzoyl-N-phenylamino)ethyl, N-(2'-pyridinyl)-N-acetylaminomethyl or N-(2'pyridinyl)-N-benzoylaminomethyl group.

6. A compound according to claim 1 wherein R is benzoylmethyl, 2-benzoylethyl, methylbenzoylmethyl, trifluoromethyl-benzoylmethyl, halobenzoylmethyl, acetoxymethyl or 2-propionylethyl.

7. A compound according to claim 1 wherein Y is methyl, ethyl, propyl, butyl, bromoethyl, bromopropyl, bromobutyl, benzyl, phenethyl, phenacyl or phenylphenacyl and X is chlorine, bromine or iodine.

* * * * *